US011911631B2

(12) United States Patent
Stauffer et al.

(10) Patent No.: US 11,911,631 B2
(45) Date of Patent: Feb. 27, 2024

(54) TUMOR BED IMPLANT FOR MULTIMODALITY TREATMENT OF AT RISK TISSUE SURROUNDING A RESECTION CAVITY

(71) Applicants: Thomas Jefferson University, Philadelphia, PA (US); Drexel University, Philadelphia, PA (US)

(72) Inventors: Paul Stauffer, Philadelphia, PA (US); Voichita Bar-ad, Wynnewood, PA (US); Mark Hurwitz, Narberth, PA (US); Adam Luginbuhl, Gulph Mills, PA (US); Michele Marcolongo, Aston, PA (US); Dario Rodrigues, Philadelphia, PA (US); David Cognetti, Penn Valley, PA (US); Joseph Curry, Wynewood, PA (US); Katsiaryna Prudnikova, Huntingdon Valley, PA (US)

(73) Assignees: Thomas Jefferson University, Philadelphia, PA (US); Drexel University, Philadelphia, PA (US)

( * ) Notice: Subject to any disclaimer, the term of this patent is extended or adjusted under 35 U.S.C. 154(b) by 0 days.

(21) Appl. No.: 16/086,733

(22) PCT Filed: Mar. 31, 2017

(86) PCT No.: PCT/US2017/025523
§ 371 (c)(1),
(2) Date: Sep. 20, 2018

(87) PCT Pub. No.: WO2017/173352
PCT Pub. Date: Oct. 5, 2017

(65) Prior Publication Data
US 2019/0099618 A1 Apr. 4, 2019

Related U.S. Application Data

(60) Provisional application No. 62/315,839, filed on Mar. 31, 2016.

(51) Int. Cl.
*A61N 5/10* (2006.01)
*A61N 2/00* (2006.01)
(Continued)

(52) U.S. Cl.
CPC .............. *A61N 5/1015* (2013.01); *A61B 5/06* (2013.01); *A61B 5/6852* (2013.01);
(Continued)

(58) Field of Classification Search
CPC .......................... A61N 5/1001–1029; A61N 2005/1003–1025; A61N 2/00–12;
(Continued)

(56) References Cited

U.S. PATENT DOCUMENTS 6,074,337 A 6/2000 Tucker et al.
6,248,057 B1 6/2001 Mavity et al.
(Continued)

FOREIGN PATENT DOCUMENTS

EP 0719571 A2 7/1996
EP 1129990 A1 9/2001
(Continued)

OTHER PUBLICATIONS

"Used." Merriam-Webster Dictionary. https://www.merriam-webster.com/dictionary/use#h1. Accessed May 31, 2023. (Year: 2023).*
(Continued)

*Primary Examiner* — Carrie R Dorna
(74) *Attorney, Agent, or Firm* — Saul Ewing LLP; Kathryn Doyle; Sean Ritchie

(57) ABSTRACT
A device having a biocompatible polymer as a body and regularly spaced radiation seeds and regularly spaced mag-
(Continued)

netic materials disposed of within the body of the biocompatible polymer, or uniformly distributed liquid radiation and magnetic fluid materials within a polymer slab, hollow thick wall polymer shell, or thin wall polymer balloon, as suitable for surgical placement within a resection cavity for treatment of at-risk tissue in the tumor margin with local hyperthermia in combination with radiation and potentially also with chemotherapy and/or immunotherapy that is slowly released from the biocompatible polymer.

18 Claims, 11 Drawing Sheets

(51) Int. Cl.
| | |
|---|---|
| *A61K 41/00* | (2020.01) |
| *A61K 51/12* | (2006.01) |
| *A61B 5/00* | (2006.01) |
| *A61B 5/06* | (2006.01) |
| *A61N 5/02* | (2006.01) |
| *A61B 5/01* | (2006.01) |

(52) U.S. Cl.
CPC ...... *A61K 41/0052* (2013.01); *A61K 51/1213* (2013.01); *A61N 2/002* (2013.01); *A61N 2/004* (2013.01); *A61N 5/025* (2013.01); *A61N 5/1027* (2013.01); *A61B 5/01* (2013.01); *A61B 5/4848* (2013.01); *A61N 2005/1024* (2013.01)

(58) Field of Classification Search
CPC .. A61N 5/1002; A61N 5/1007; A61N 5/1014; A61N 5/1015; A61N 2005/1004; A61N 2005/1005; A61N 2005/1008; A61N 2005/1022; A61N 2005/1024; A61N 2005/1025; A61K 41/0052; A61F 2007/009; A61F 7/123
See application file for complete search history.

(56) References Cited

U.S. PATENT DOCUMENTS

| | | | |
|---|---|---|---|
| 6,527,693 B2 | 3/2003 | Munro, III et al. | |
| 6,589,502 B1 | 7/2003 | Coniglione et al. | |
| 6,641,519 B1 | 11/2003 | Kindlein et al. | |
| 6,761,680 B2 | 7/2004 | Terwilliger et al. | |
| 2003/0088145 A1 | 5/2003 | Scott | |
| 2003/0097035 A1 | 5/2003 | Tucker et al. | |
| 2004/0109823 A1 | 6/2004 | Kaplan | |
| 2004/0167506 A1* | 8/2004 | Chen ...... | A61B 18/04 606/27 |
| 2004/0242953 A1 | 12/2004 | Good | |
| 2005/0021088 A1* | 1/2005 | Schuler ...... | A61B 18/04 607/1 |
| 2006/0100475 A1* | 5/2006 | White ...... | A61N 5/1015 600/3 |
| 2007/0173680 A1* | 7/2007 | Rioux ...... | A61B 18/148 600/2 |
| 2008/0146861 A1* | 6/2008 | Murphy ...... | A61N 5/1015 600/3 |
| 2008/0146862 A1* | 6/2008 | Cutrer ...... | A61N 5/1015 600/7 |
| 2008/0228025 A1 | 9/2008 | Quick | |
| 2009/0054721 A1* | 2/2009 | Martin ...... | A61N 5/1015 600/4 |
| 2009/0131735 A1 | 5/2009 | Drobnik et al. | |
| 2012/0083740 A1 | 4/2012 | Chebator | |
| 2012/0130362 A1* | 5/2012 | Hastings ...... | A61B 18/04 606/33 |
| 2013/0261368 A1 | 10/2013 | Schwartz | |
| 2014/0257013 A1 | 9/2014 | D'Andrea | |
| 2014/0378739 A1 | 12/2014 | Munro, III et al. | |
| 2015/0010470 A1 | 1/2015 | Kaplan | |
| 2015/0126990 A1 | 5/2015 | Sharma et al. | |
| 2015/0057487 A1 | 6/2015 | Nakaji et al. | |
| 2015/0265849 A1 | 9/2015 | Krechting | |
| 2017/0065324 A1* | 3/2017 | Attaluri ...... | A61B 18/04 |
| 2018/0304100 A1 | 10/2018 | Bharat et al. | |

FOREIGN PATENT DOCUMENTS

| | | |
|---|---|---|
| JP | 4-116146 A | 4/1992 |
| JP | 6-508278 | 9/1994 |
| JP | 9-122260 | 5/1997 |
| JP | 2001-262343 A | 9/2001 |
| JP | 2001518818 A | 10/2001 |
| JP | 2010233682 A | 10/2010 |
| JP | 2012-75892 A | 4/2012 |
| JP | 2014-516614 A | 7/2014 |
| WO | 9222350 A1 | 12/1992 |
| WO | 9844980 A1 | 10/1998 |
| WO | 2008076512 A2 | 6/2008 |
| WO | 2013/106052 A2 | 7/2013 |
| WO | WO 2014065666 A1 | 5/2014 |
| WO | WO 2015181632 A1 | 12/2015 |
| WO | WO 2016163885 A1 | 10/2016 |

OTHER PUBLICATIONS

Extended European Search Report, European Patent Application No. 17776835.5, dated Jan. 2, 2020.
International Search Report and Written Opinion, International Patent Application No. PCT/US2017/025523; dated Aug. 1, 2017.
Gautam, B., et al., "Practical considerations for maximizing heat production in a novel thermobrachytherapy seed prototype", Med. Phys. 41 (2), Feb. 2014, pp. 023301-1-023301-10.
Kouloulias, V., et al., "Combined chemoradiotherapy with local microwave hyperthermia for treatment of T3NO laryngeal carcinoma: a retrospective study with long-term follow-up", ACTA otorhinolaryngologica ita lica 2014;34:167-173.
Arunachalam, K., et al., "Preclinical assessment of comfort and secure fit of thermobrachytherapy surface applicator (TBSA) on volunteer subjects", Journal of Applied Clinical Medical Physics, vol. 13, No. 5, 2012, 13 pages.
Arunachalam, K., et al., "Thermal characteristics of thermobrachytherapy surface applicators for treating chest wall recurrence", Phys. Med. Biol. 55 (2010) 1949-1969.
Mack, C. F., et al., "Interstitial Thrmoradiotherapy With Ferromagnetic Implants for Locally Advanced and Recurrent Neoplasms", Inl J Radiation Oncology Biol Phys., 1993, vol. 27. pp. 109-115.
Sneed, P. K., et al., "Survival Benefit of Hyperthermia in a Prospective Randomized Trial of Brachytherapy Boost +/- Hyperthermia for Glioblastoma Multiforme", Inl J Radiation Oncology Biol Phys., vol. 40, No. 2, pp. 287-295, 1998.
Arunachalam, K., et al., "Progress on ThermoBrachytherapy Surface Applicator for Superficial Tissue Diseases", In Proc. SPIE, Feb. 12, 2009.
Stauffer, P. R., et al., "Magnetic Induction Heating of Ferromagnetic Implants for Inducing Localized Hyperthermia in Deep-Seated Tumors", IEEE Transactions on BIOMedical Engineering, vol. BME-31, No. 2, Feb. 1984, pp. 235-251.
Stauffer, P. R., et al., "Observations on the Use of Ferromagnetic Implants for Inducing Hyperthermia", IEEE Transactions on BIOMedical Engineering, vol. BME-31, No. 1, Jan. 1984, pp. 76-90.
Stauffer, P. R., et al., "Progress on System for Applying Simultaneous Heat and Brachytherapy to Large-Area Surface Disease", Proceedings of SPIE vol. 5698 (SPIE, Bellingham, WA, 2005), pp. 82-96.
Stauffer, P. R., et al., "Tumor bed brachytherapy for locally advanced laryngeal cancer: a feasibility assessment of combination with ferromagnetic hyperthermia", Biomed. Phys. Eng. Express 2 (Sep. 8, 2016), 12 pages.
Osintsev, A., et al., "Preliminary Tests of Local Hyperthermia Based on Inductively Heated Tumor Bed Implant", Science Evolution, Jan. 2017, vol. 2, No. 2, 8 pages.

(56) References Cited

OTHER PUBLICATIONS

Atkinson, W. J., et al., "Usable Frequencies in Hyperthermia with Thermal Seeds", IIEEE Transactions on BIOMedical Engineering, vol. BME-31, No. 1, Jan. 1984, pp. 70-75.

Attaluri, A., et al., "Nanoparticle distribution and temperature elevations in prostatic tumours in mice during magnetic hanoparticle hyperthermia", Int. J. Hyperthermia, Aug. 2011; 27(5): 491-502.

Cetas, T. C., et al., "A Ferrite Core/Metallic Sheath Thermoseed for Interstitial Thermal Therapies", IEEE Transactions on BIOMedical Engineering, vol. 45, No. 1, Jan. 1998, pp. 68-77.

Gautam, B., et al., "Dosimetric and thermal properties of a newly developed thermobrachytherapy seed with ferromagnetic core for treatment of solid tumors", Medical Physics vol. 39, No. 4, Apr. 2012, pp. 1980-1990.

Gneveckow, U., et al., "Description and characterization of the novel hyperthermia- and thermoablation-system MFH@300F for clinical magnetic fluid hyperthermia", Med. Phys. 31 (6), Jun. 2004, pp. 1444-1451.

Johannsen, M., et al., "Magnetic nanoparticle hyperthermia for prostate cancer", Int. J. Hyperthermia, Dec. 2010; 26(8): 790-795.

Jordan, A., et al., "Magnetic Nanoparticles for Cancer Therapy", Physics of Thermal Therapy, 2013, pp. 293-318.

Maier-Hauff, K., et al., "Intracranial thermotherapy using magnetic nanoparticles combined with external beam radiotherapy: Results of a feasibility study on patients with glioblastoma multiforme", J Neurooncol (2007) 81:53-60.

Maier-Hauff, K., et al., "Efficacy and safety of intratumoral thermotherapy using magnetic iron-oxide nanoparticles combined with external beam radiotherapy on patients with recurrent glioblastoma multiforme", J Neurooncol (2011) 103:317-324.

Parsai E. I., et al., "Evaluation of a Novel Thermobrachytherapy Seed for Concurrent Administration of Brachytherapy and Magnetically Mediated Hyperthermia in Treatment of Solid Tumors", J Biomed Phys Eng 2011; 1(1), pp. 5-16.

Paulus, J. A., "Thermal Ablation of Canine Prostate Using Interstitial Temperature Self-Regulating Seeds: New Treatment for Prostate Cancer", Journal of Endourology vol. 11, No. 4, Aug. 1997. pp. 295-300.

Warrell G., et al., "Use of novel thermobrachytherapy seeds for realistic prostate seed implant treatments", Med. Phys. 43 (11), Oct. 19, 2016, pp. 6033-6048.

Master, A., et al., "Ferromagnetic thermal ablation of locally recurrent prostate cancer: prostate specific antigen results and immediate/intermediate morbidities", J Urol. Dec. 2004; 172(6 PI 1) 2197-202, Abstract.

Inatomi, H., et al., "Thermal distribution in the agar phantom by a new intracavitary RF applicator for prostate gland", J UOEH Mar. 1, 1992; 14(1) 39-45, Abstract.

Diederich, C. J., et al., "Direct-coupled interstitial ultrasound applicators for simultaneous thermobrachytherapy: a jeasibility study", Int. J. Hyperthermia, 1996, vol. 12, No. 3,401-419.

Dvorák, J., et al., "Endovascular brachytherapy potentiated by hyperthermia in the prevention of vascular restenosis", Cardiovascular Radiation Medicine 2 (2001) 205- 207.

Furuta, M., et al., "Simultaneous Intraluminal Thermobrachytherapy: An in vitro Study", Jpn. J. Cancer Res. 92, 904-910, Aug. 2001.

Prionas, S. D., et al., "Thermometry of Interstitial Hyperthermia Given as an Adjuvant to Brachytherapy for the Treatment of Carcinoma of the Prostate", Int J. Radiation Oncology Biol. Phys., 1993, vol. 28, pp. 151-162.

Rafla, S., et al., "Recurrent Tumors fo the Head and Neck, Pelvis, and Chest Wall: Treatment with Hyperthermia and Brachytherapy", Radiology 1989; 172:845-850.

Shinohara, K., "Thermal ablation of prostate diseases: advantages and limitations", Int. J. Hyperthermia, vol. 20, No. 7 (Nov. 2004), pp. 679-697.

Van Haaren, P. M. A., et al., "Reliability of temperature and SAR measurements at oesophageal tumour locations", Int. J. Hyperthermia, Nov. 2006; 22(7): 545-561.

Juilgol, N. G., et al., "Chemoradiation with hyperthermia in the treatment of head and neck cancer", International Journal of Hyperthermia: 26(1), Feb. 2010, 21-25.

Jha, S., et al., "Hyperthermia: Role and Risk Factor for Cancer Treatment", Achievement in the Life Sciences: vol. 10, Issue 2, Dec. 2016, 161-167.

Notice of Reasons for Rejection, Japanese Patent Application No. 2018-551372, dated Mar. 18, 2021.

communication, Partial European Search Report, European Patent Application No. 21183933.7, dated Jan. 14, 2022.

Official Action, Israel Patent Application No. 261962, dated Feb. 9, 2022.

Notice of Reasons for Rejection, Japanese Patent Application No. 2018-551372, dated Feb. 7, 2022.

Communication, Extended European Search Report, European Patent Application No. 21183933.7, dated Apr. 14, 2022.

\* cited by examiner

TUMOR BED IMPLANT FOR MULTIMODALITY TREATMENT OF AT RISK TISSUE SURROUNDING A RESECTION CAVITY

CROSS-REFERENCE TO RELATED APPLICATIONS

This application is a national phase application under 35 U.S.C. 371 of International Application No. PCT/US2017/025523, filed Mar. 31, 2017, which claims priority to U.S. Provisional Patent Application Ser. No. 62/315,839, filed Mar. 31, 2016. The entire content of each application is hereby incorporated by reference herein.

FIELD OF INVENTION

The disclosed embodiments are related to biocompatible implant devices suitable for surgical placement within a resection cavity for treatment of at-risk tumor margin tissue with local hyperthermia in combination with radiation and/or chemotherapy and/or immunotherapy.

BACKGROUND OF INVENTION

In the treatment of cancer, tumors are generally removed surgically when possible and surgery is often followed by radiation therapy (RT) of the region. RT is intended to sterilize, kill, or damage, disease left dispersed within the unresected tumor margin. In the case of tumor recurrence, surgical excision of tumor regrowth may be the best option again, but usually a second tumoricidal radiation dose is not possible without unacceptable complications in surrounding normal tissues. Regardless of resection volume, tissues immediately surrounding the excised tumor volume are at risk for tumor regrowth from remaining microscopic disease. One method of concentrating radiation in tissues at risk and minimizing dose to surrounding normal tissues is to place radioactive sources directly inside the resection cavity to radiate tissue from the inside out. With appropriate activity level and duration in tissue, this procedure delivers the appropriate dose of radiation slowly over a period of time, and is thus called Brachytherapy. This procedure may be used to deliver radiation to tumor or at-risk tissue in close vicinity to small radiation sources that are generally implanted through one or more interstitial needles or plastic catheters, or through an endoluminal catheter or instrument inserted into a balloon or natural body orifice. Brachytherapy sources may be distributed within the target tissue in the form of one or more parallel preconfigured strings of radioactive small diameter cylindrical seeds placed in the resection cavity or inserted into afterloading catheters that are placed percutaneously into the tumor region in a planar or volumetric implant array. Alternatively, a single radiation source of very high activity located at the end of a wire may be pulled in computer controlled incremental steps through each implanted catheter, where the pause duration at each step is calculated to deliver the proper radiation dose before moving to the next point.

One problem of the existing protocols for treating tumor bed tissue with small radiation sources is the non-uniform radiation dose around seed strings that are sewn directly to the tissue wall of tumor resection cavities with irregular shape. As seen in FIG. 1, there is a very rapid exponential falloff of radiation dose with radial distance from the surface of each small (~1 mm) diameter seed and seeds are generally spaced ~5 mm apart along each string. This produces a highly non-uniform dose distribution along the length of the seed string. In addition, the seed strings are placed 1 cm or more apart so there is an even higher dose falloff between adjacent seed strands. In order to get a high enough minimum dose between seeds and at the desired distance into tissue (e.g., 5 mm distance into surrounding at-risk tissue), the peak radiation dose in tissue adjacent to the seeds is extremely high, which risks complications when seeds are placed near critical normal tissues. Indeed, doses of up to 500% above the minimum prescribed target tissue dose are delivered at the seed surface, but quickly reduce towards non-therapeutic levels with increasing distance from the seed. Accordingly, the prior art treatments risk both radiation necrosis from overdosing as well as under dosing of other tissue within the same treatment target, which reduces efficacy of the treatment.

A second issue is related to normal tissue toxicity. In the existing protocols, the seed string is inserted or even sutured in place within the tumor bed, often with additional transplanted tissue flaps (i.e. fat or muscle tissue excised from elsewhere in patient) to separate the seeds from nearby critical normal tissues. The transplanted tissue acts as a spacer, but the thickness of the transplant often varies significantly within a single slab. This has a direct effect on the radiation dose distribution delivered to surrounding at-risk tumor margin. Moreover, the transplanted tissue may have weak structure that does not always control the separation distance from seeds to tumor margin or the migration of seeds during the brachytherapy delivery adequately. When seeds move during the implant period, which can last anywhere from 1 hour to >50 days, this causes distortion of the expected dose distribution with unanticipated excessive dose in regions where seeds bunch together and underdosing of locations where seeds drift away from initial positions.

Surgical resection may be the treatment of choice for tumors located almost anywhere in the body, including head and neck, brain, lung, breast, torso and extremities. One typical location for tumors amenable to treatment with the proposed invention are tumors of the head and neck. Integration of new treatment approaches for head and neck cancers such as organ preservation surgery (1, 2), high-dose-rate brachytherapy (3), chemotherapy (4, 5), immunotherapy (6-8), and hyperthermia (9-11) have been proposed to enhance clinical outcomes. Local tumor hyperthermia at temperatures of 41-45° C. for 30-60 min is one of the most promising adjuvant treatment methods in cancer therapy, contributing to a significant improvement of therapeutic efficacy in sites where adequate heating is possible. It is normally applied as an adjuvant to established cancer treatment modalities such as radiotherapy and/or chemotherapy (12-14), and is currently being investigated for potential synergism and activation of immunotherapy. (15-17).

Chemotherapy treatments are well known and there are numerous methods of delivering chemotherapeutics to human tumors; the optimum method depends on site and tumor size among other factors. Drug delivery is perhaps most dependent on tumor vasculature which is widely variable across a tumor volume and often compromised in the center of large or rapidly growing tumor masses. While chemotherapy is generally administered systemically with good effect, in many solid tumors the local concentration is inadequate at levels considered toxic to critical normal tissues. In some tumors, local concentration of therapeutic may be increased using a liposomal formulation where the active drug is carried inside a lipid outer layer that reduces accumulation of therapeutic in critical normal tissues like heart, liver and spleen. This local drug delivery scheme can be further enhanced using a temperature sensitive liposome formulation that breaks down the lipid capsule at a moderate hyperthermic temperature (e.g. 40° C.) and releases the cytotoxic drug into the heated tumor tissue. (18-21). Alternatively, drug may be instilled directly into a body cavity for more concentrated effect on adjacent tissue. One example of this approach is the treatment of non-muscle invasive bladder cancer and the local effect can be increased further by the addition of local hyperthermia. (22-24). For tumors located in the brain, there are additional problems getting drugs to cross the blood brain barrier. One approach for brain tumors that can be surgically removed is to attach biodegradable thin polymer "wafers" that are impregnated with the desired therapeutic (e.g. carmustine, BCNU, Gliadel wafer) all around the inside of the resection cavity to release drug directly into surrounding tissue, thereby bypassing blood vessels and the blood brain barrier. (25, 26).

In head and neck treatments, such as in the Larynx, microwave radiation is often used to produce local hyperthermia of tumors located close to the skin surface, but penetration of effective heating is limited to about 3-4 cm. Treatment of tumors deep in the neck with external microwave waveguide applicators has been reported, but significant heating of overlying tissue is unavoidable (27, 28). Penetration deeper into tissue using a phased array of microwave antennas has been proposed (29, 30) and prototype arrays are currently under development (10, 31), but it remains a challenge to precisely focus heat within the human head without overheating surrounding critical normal tissues. Similarly, radiofrequency annular phased array systems are available (32-34) that can penetrate deeper in the body, but the long wavelength produces a large heat focus and significant sidelobe heating in surrounding normal tissues. In either case, significant heating of critical normal tissues outside the intended tumor target is usually unavoidable. Ultrasound from external transducer arrays may be focused precisely into deep tissue targets (35-39), but this approach is problematic for head and neck tumors such as the larynx due to the heterogeneous anatomy and proximity to complex shaped air and bone regions that reflect or absorb ultrasound preferentially. Thus, while there are numerous external electromagnetic and ultrasound heating devices available, the complex anatomy and sensitivity of surrounding critical normal tissues severely restrict the use of external heating technology for small head and neck tumors like the larynx.

Alternatively, improved localization of heat within a small volume at depth may be obtained with a variety of internal heat source techniques, including interstitial radiofrequency electrodes, microwave antennas, ultrasound transducers, or one of several thermal conduction based hot source techniques (40). Most of these interstitial heating modalities require percutaneous insertion of an array of needles or catheters to insert heat sources, power connections, and temperature monitoring/control sensors into the tumor. For many head and neck tumors including nasopharynx and larynx, maintaining an externalized array of percutaneous catheters following surgery is painful and undesirable for the patient. Thus for tumors in the head and neck region, one hot source technique stands out as potentially most appropriate for minimally invasive local hyperthermia. The use of external magnetic fields to inductively couple energy into implanted ferromagnetic material has been investigated by numerous groups beginning almost 45 years ago (41-45). Early studies focused on coupling energy into ferromagnetic needles, spheres, and small diameter ferroseeds placed into solid tumors via an array of 1-1.5 cm spaced plastic catheters (46-48). More recently, work has accelerated on the use of magnetic nanoparticles (49-53) that may be delivered either systemically or injected directly into the tumor. When any of these materials are immersed in a sub-megahertz radiofrequency magnetic field, power is absorbed by the ferromagnetic material and tissue around the implants is heated by thermal conduction from the hot material into surrounding cooler tissue. Because of the rapid falloff of temperature away from the small diameter ferromagnetic implants (especially in tissue with good blood perfusion), there are steep temperature gradients around the implants. Tissue directly adjacent to the magnetically coupled heated material is generally overheated, while tissue>5 mm from the hot sources may not be heated sufficiently (45, 54). One method of improving the control of temperature within an array of ferromagnetic implants is to use materials that undergo their Curie point transition from magnetic to non-magnetic state at the desired implant temperature (42, 44, 55). These ferroseeds self-regulate their temperature at approximately the Curie point of the alloy regardless of applied power level, leading to more uniform tumor heating without the need to measure internal source temperatures or adjust power of the external magnetic field.

Clinical trials have shown that when sufficient heating of tumor is accomplished (minimum target temperature around 41-45° C. for 60 min treatment), the response rate to radiation and/or chemotherapy is significantly enhanced. (14, 56). Data has also demonstrated that significantly higher thermal enhancement of radiation response is achieved when the heat and radiation treatments are applied simultaneously (57, 58). Existing technology for heating tumor bed in combination with radiation is limited to interstitial radiofrequency (RF), microwave, or ultrasound sources placed in needles or catheters implanted in or around the tumor bed. These invasive sources must be connected to external equipment with multiple power and thermal monitoring probe connections through the skin, with obvious discomfort and inconvenience for the patient.

There is increasing interest in the use of inductive heating of superparamagnetic (subdomain) nanoparticles which may be administered systemically or injected directly into the tumor (49, 50, 53, 59, 60). The challenges for systemic delivery are the low concentration and uneven distribution of magnetic nanoparticles due to heterogeneous blood flow and irregular release of particles in tumor tissue. The low density of magnetic material that accumulates in the tumor requires a high magnetic field strength (over $10^4$ A/m at 100 kHz), which may cause treatment limiting non-specific eddy current heating of normal tissues that overshadows the heating of low density magnetic particles. While direct injection of nanoparticles into the tumor produces a high concentration of particles along each needle injection site, diffusion of particles into tissue between injection sites is generally poor, leading to highly uneven distribution of particles and thus heterogeneous tissue temperatures. Still, some clinical benefit has been reported using multiple needle injections of magnetic nanoparticles in parallel tracks to heat tissue by thermal conduction between the injection tracks (51, 61, 62).

Correspondingly, while brain tumors are head and neck tumors, they present additional challenges for heating technologies because the brain is surrounded by a thick layer of protective bone (skull). Recent advances in MR guided focused ultrasound (MRgFUS) have encouraged research into external multi-element transducer arrays that can focus energy into small volumes at depth in brain. (63). Currently approved clinical indications for MRgFUS in the US are limited to treatment of essential tremor, neuropathic pain, and Parkinson's disease as these diseases tend to involve small volumes of tissue located closer to the center of the skull where better focal gain can be obtained from the surface conforming transducer array.(64) Techniques to treat brain tumors that tend to be larger and located off center closer to the skull are currently under investigation.

To date, heat treatment of brain tumors has been accomplished primarily with interstitially implanted heat sources that are able to localize power deposition at depth below the skull. Several investigators implanted 1-2 cm spaced arrays of miniature (1-2 mm dia) coaxial cable dipole microwave antennas for heating brain tumors in combination with interstitial brachytherapy. (65, 66) Satoh et al. (67, 68) developed an adjustable length helical coil microwave antenna specifically for localizing heat in brain tumors that could be implanted with a 3-7 catheter array for combination interstitial heat and I-125 brachytherapy. Subsequent clinical investigations from the same group completed a randomized trial of brachytherapy boost+/−interstitial microwave hyperthermia for treatment of glioblastoma multiforme and demonstrated a statistically significant improvement in 2 year local control.(69-71) Separately, Stea et al. (27, 72, 73) demonstrated a significant increase in 1 year survival for patients with supratentorial gliomas treated with adjuvant interstitial hyperthermia generated with 1 cm spaced arrays of implanted ferromagnetic seeds coupled to an external magnetic field. Clinical studies are now underway treating glioblastoma with interstitially implanted trails of iron oxide nanoparticles coupled to external magnetic field and combined with external beam radiation therapy. (51, 61, 62)

Accordingly, the present application describes new therapeutic devices and methods for treatment of certain cancers, specifically those in the head and neck, brain, and other sites that produce a resection cavity, including but not limited to cancers of the chest and abdomen, pelvis, arms and legs—sites where resection of a mass can be treated according to the inventions disclosed herein.

SUMMARY OF INVENTION

The objective of the present invention is directed to a multimodality therapeutic device and methods for using the same for treating cancerous cells that remain after tumor surgery, with lower toxicity to surrounding normal tissues than existing clinical approaches. The specific purpose is to create a product that will improve dose uniformity—by increasing minimum dose to the target while reducing treatment complications in normal tissues surrounding a tumor resection cavity, and thereby improve clinical outcomes and overall experience for the cancer patient.

In particular embodiments, the device is directed to treating tissue in the tumor margin of surgical resection cavities with brachytherapy, and optionally combined with local hyperthermia. In alternative embodiments, chemotherapy and/or immunotherapy can be utilized alone or with the brachytherapy and/or the hyperthermia, whereby all treatments are delivered from a biocompatible resection cavity shaped multimodality tumor bed implant inserted at the time of surgery.

A further embodiment of this invention is to provide improved thermobrachytherapy treatment of recurrent cancer from within a tumor bed-shaped implant that contains both permanent radioactive seeds to deliver a well-localized radiation dose around the implant, and magnetic material that produces mild heating of tissue when immersed in an external magnetic field, to enhance the efficacy of radiation treatment.

A further embodiment is directed to a method of organ-preserving brachytherapy treatment for locally advanced head and neck tumors, and a specific example is given for treatment of patients with laryngeal squamous cell carcinoma, comprising inserting a therapeutic device comprising a therapeutic within a biocompatible polymer and a magnetic or ferrous material capable of being heated by an external heat source; and heating said therapeutic device with an external source.

A further embodiment is directed to tumor bed implants made from a biocompatible resorbable polymer that contains brachytherapy seeds interspersed with ferromagnetic seeds intended for permanent implantation in the patient. The polymer layer covering the seeds should improve the dosimetry of post-surgical thermobrachytherapy and subsequently break down in tissue following completion of the intended treatment, in order to minimize possibility of long-term rejection by the body and/or reduce local swelling and bulk in the region.

A further embodiment is directed to biocompatible non-resorbable polymer tumor bed implants containing permanent brachytherapy seeds interspersed with ferromagnetic seeds. This format should improve the dosimetry of post-surgical thermobrachytherapy in cancer patients and also preserve implant volume after surgery to avoid an undesirable tissue defect in sites like breast, extremity sarcoma, and brain.

A further embodiment is directed to biocompatible resorbable polymer implants containing magnetic, chemotherapeutic and/or immunotherapy agents incorporated within the polymer suitable for heating the at-risk tissue around the resection cavity 1-10 times at the same time as heating the polymer to the point of at least partial degradation and rapid release of therapeutics into surrounding tissue when the implant is immersed in an external magnetic field.

A further embodiment is directed to biocompatible resorbable polymer implants containing chemotherapeutic and/or immunotherapy agents incorporated within the polymer in addition to magnetic materials intended for heating the resection cavity wall 1-10 times when immersed in an external magnetic field in combination with external beam radiation therapy. In this embodiment, the polymer would remain intact throughout the series of thermally enhanced external beam radiation treatments, and begin a slow degradation thereafter to slowly release therapeutics into the at-risk tissues around the resection cavity at a safe time interval after completion of radiation.

A further embodiment is directed to a biocompatible thin layer polymer "balloon" implant intended for combined thermobrachytherapy treatment of surrounding tissues at risk. The balloon is elastic in order to stretch to fill a tumor resection cavity when filled with a radioactive fluid mixed with magnetic nanoparticles. This strategy provides highly uniform radiation and thermal dose distributions around the surface of the polymer balloon implant.

A further embodiment is directed to a biocompatible polymer implant that consists of two concentric thin elastic layers that can be filled with two different fluids—the inner balloon to be filled with inexpensive saline or liquid polymer while the outer balloon in contact with the resection cavity wall contains the radioactive fluid mixed with magnetic nanoparticles to provide highly uniform radiation and thermal dose distributions in tissue around the surface of the polymer implant.

A further embodiment is directed to a biocompatible thin layer polymer balloon implant that contains one or more internal catheters that extend from the tip of the balloon to outside the skin surface in order to afterload a radioactive source(s) into the balloon in combination with magnetic nanoparticles dispersed uniformly within the balloon.

A biocompatible polymer core brachytherapy device comprising: a biocompatible polymer core and radioactive seeds, wherein said radioactive seeds are regularly spaced on or under the surface of said biocompatible polymer, wherein said device provides a radiation dose delivered to tissue surrounding the device when implanted in tumor bed following tumor resection. In certain embodiments, the polymer core is fabricated from a one or more component viscous fluid mixture that gels at about body core temperature to form a soft solid implant in the shape of a tumor resection cavity and the polymer is resorbable in biologic tissue over an extended time period. In other embodiments, the biocompatible polymer core is non-resorbable to maintain equal volume and shape after implantation in the tumor bed; yet in other embodiments, the polymer core is resorbable in biologic tissue over an extended time period and an immune stimulating compound is incorporated within the polymer for slow release into surrounding tumor bed as the polymer core resorbs.

A thermobrachytherapy implant device comprising a biocompatible polymer core, radiation seeds, and magnetic materials, wherein the magnetic materials are distributed under the surface or within said polymer core, and wherein said device provides a combination of both brachytherapy radiation and hyperthermia doses delivered to tissue surrounding the device when implanted in tumor bed following tumor resection. Preferable the the magnetic materials are cylindrical seeds or spherical pellets, regularly spaced and interspersed with radiation seeds under the surface of polymer core and the radiation seeds are short half-life radioactive seeds suitable for permanent implantation in the body to deliver a desired therapeutic dose of radiation to tissues close to the seed implant in combination with heat from the ferromagnetic materials. In preferred embodiments, the magnetic materials have a Curie point transition from magnetic to non-magnetic at a desired implant temperature, e.g. between 40-100° C. and preferable between 40-50° C.

A multimodal implant device comprising a biocompatible polymer core, a therapeutic agent selected from the group consisting of a chemotherapeutic or immunotherapeutic, or combinations thereof, and magnetic materials, wherein the magnetic materials are embedded within said polymer core, and wherein said device provides a combination of chemotherapy and hyperthermia delivered sequentially or simultaneously to tissue surrounding the device when implanted in a tumor bed following tumor resection.

A multimodality treatment device comprising a biocompatible elastic or expandable polymer shell having an outer and inner surface and comprising regularly spaced radioactive seeds and magnetic materials embedded adjacent to the inner surface of said expandable polymer shell, and a polymer core within said polymer shell. Preferably the magnetic material is selected from the group consisting of: ferromagnetic cylindrical seeds, spherical pellets, particles, nanoparticles, ferrofluid, or combinations thereof, with a Curie point transition from magnetic to non-magnetic at a desired implant temperature in the range of 40-70° C. Depending on the therapeutic use, the the polymer shell is resorbable or non-resorbable, allowing for release of therapeutics into the surrounding tissue, or to support the tissue with the non-resorbable material. In certain embodiments, a material is injected between the inner and outer surface so as to expand the outer surface to fill the resection cavity.

A multimodality implant device comprising a biocompatible expandable thin wall polymer shell with a hollow central core, radioactive and magnetic materials, and wherein the polymer shell is capable of expanding to fill a tumor resection cavity. In certain embodiments, a material is injected into the core to expand the outer polymer shell to fill a tumor resection cavity, such as saline, a biocompatible resorbable liquid polymer, a biocompatible non-resorbable liquid polymer, a radioactive fluid suitable for permanent implantation in the body (e.g. Iotrex, Cesitrex), a biocompatible uniformly distributed magnetic nanoparticle solution, such as iron oxide nanoparticles with dextran, or combinations thereof. The material may further comprise a chemotherapeutic agent or liposome encapsulated therapeutic drug, or an immune stimulating agent.

A multimodality treatment device comprising a biocompatible expandable polymer shell balloon, wherein the polymer shell is capable of expanding to fill a tumor resection cavity, a radioactive material, a magnetic material, a hollow central space containing one or more catheters, and a flexible shaft connecting the balloon implant to the tissue surface. The device comprises at least one catheter extending from outside the skin surface to the tip of polymer shell and allows remote afterloading insertion of a High-Dose-Rate (HDR) brachytherapy source into the central space inside the polymer shell and preferable one or more catheters extend from outside the skin surface to various locations inside the hollow space of the polymer shell to allow insertion of temperature monitoring probes and for filling the interior space with fluids, such as a magnetic nanoparticle solution.

A multimodality treatment device comprising a first biocompatible expandable polymer shell balloon, and a second polymer shell; wherein the first and second polymer shells are capable of expanding to fill a tumor resection cavity, a radioactive material, a magnetic material, a hollow central space containing one or more catheters within the second polymer shell, and a void between the first and second polymer shells, and a flexible shaft connecting the balloon implant to the tissue surface. A first fluid is injected into the hollow central space and a second fluid is injected into the void between the first and second polymer shells.

The above identified devices can be utilized in methods of treatment of cancerous cells, by inserting the devices into a resection cavity and placing them adjacent to said cells. Preferably the method further comprises coupling energy into said device from an external magnetic field so as to heat the magnetic materials which thereby heat the surrounding tumor bed tissue.

A further method of treating a cancerous tissue inside a body comprising: removing a portion of the cancerous tissue thereby leaving a resection cavity in the body, inserting into said resection cavity a device as provided above having a polymer core, using at least one additional piece of pre-gelled polymer to provide additional spacing between the polymer core and the surrounding tumor resection cavity wall; injecting viscous liquid polymer around the core implant that will solidify to hold the thermobrachytherapy delivering device in appropriate position centered within the resection cavity. Preferable the method further comprises the step of coupling energy into said device with an external magnetic field so as to heat up said device.

A further embodiment is directed towards a method of treating a cancerous tissue in a body comprising: removing a portion of the cancerous mass, thereby leaving a resection cavity in the body, inserting into said resection cavity a device a provided above having a polymer shell and a hollow central space; and filling said hollow central space with an expandable material comprising radiation and ferrous materials, so as to expand and fill the resection cavity with said thermobrachytherapy device; and coupling energy into said device with an external magnetic field so as to heat up said device.

A method of treating a cancerous tissue in a body comprising: removing a portion of the cancerous mass, thereby leaving a resection cavity in the body, inserting into said resection cavity a device as provided above comprising an elastic polymer layer configured to create a hollow central core, a chemotherapeutic, radiation, and ferrous material, wherein the hollow central core is filled with an expandable material so as to expand and fill the resection cavity with said device; and coupling energy into said device with an external magnetic field so as to heat up said device and thereby improve the local delivery of chemotherapeutics and sensitize surrounding tumor bed tissue to radiation, drugs, and immune stimulating treatments over an extended period of time.

A method of treating a tissue region inside a body containing cancer cells comprising contacting said target tissue with a multimodality implant device, wherein said device comprises a polymer core, radiation seeds, chemotherapy and or immunotherapy agents, and magnetic materials; and coupling energy into said device from an external magnetic field so as to heat the ferromagnetic materials which thereby heat the surrounding tumor bed tissue.

A method of treating a tissue region inside a body containing cancer cells comprising contacting said target tissue with a multimodality implant device, wherein said device comprises a polymer core, radiation seeds and ferromagnetic materials as described above; and coupling energy into said device from an external magnetic field so as to heat the ferromagnetic materials which thereby heat the surrounding tumor bed tissue, and radiating tissue in the vicinity of the implant device with external beam radiation, either before, during, or after release of therapeutics from the polymer core.

BRIEF DESCRIPTION OF THE DRAWINGS

FIG. 3A shows a single plane implant with multiple parallel strands of radiation seeds; FIG. 3B shows a large resection cavity implant with seeds distributed uniformly all around the outside shell of polymer core with 3-10 mm of polymer coating over the seeds to separate from tissue.

FIG. 4A shows a single plane implant with multiple parallel strands of radiation and ferroseeds; FIG. 4B shows a large resection cavity implant with seeds distributed uniformly all around the outside shell of polymer core with 3-10 mm of polymer coating over the seeds to separate from tissue, with radiation and ferroseeds alternating along each line of seeds, or alternatively with interspersed parallel strands of all radiation seeds and all ferroseeds.

FIG. 12B provides similar heat and radiation to the resection cavity wall with the addition of a temperature sensor that can be pulled along a catheter track just inside the outer balloon wall and along the flexible sheath.

DETAILED DESCRIPTION OF THE PREFERRED EMBODIMENTS

As used herein the term "about" means within 10% of a stated number.

The term "magnetic nanoparticles" is used interchangeably with magnetic fluid, or MNP fluid, are particles that can be manipulated using magnetic fields. These particles preferably are capable of being heated by application of an external force.

The term "ferromagnetic seeds" or "ferroseeds" or "heat seeds" are meant to be spherical or cylindrical metallic materials. These may be individual seeds or combined on a string of ferromagnetic seeds, or combined on a string with ferromagnetic and radiation seeds.

In a general sense, the embodiments disclosed herein define an implant device that capitalizes on the effects of mild hyperthermia (heating for 30-60 min at 40-45° C.) combined with radiation and/or chemotherapy and/or immunotherapy and focused on the annular rim of at-risk tissue around a tumor resection cavity. Randomized trials of combined thermoradiotherapy and thermochemotherapy have demonstrated significant improvement of complete response rates with the addition of local hyperthermia, as well as a survival advantage in many tumor sites. (56). Hyperthermia is particularly efficacious in the re-treatment setting where radiation dose is limited. (14, 15). The typical problem restricting use of hyperthermia is poor control of power deposition pattern from the heat source which produces unacceptable heterogeneity of temperatures across the tissue target and unacceptable heating of surrounding normal tissues.

Figure 1:
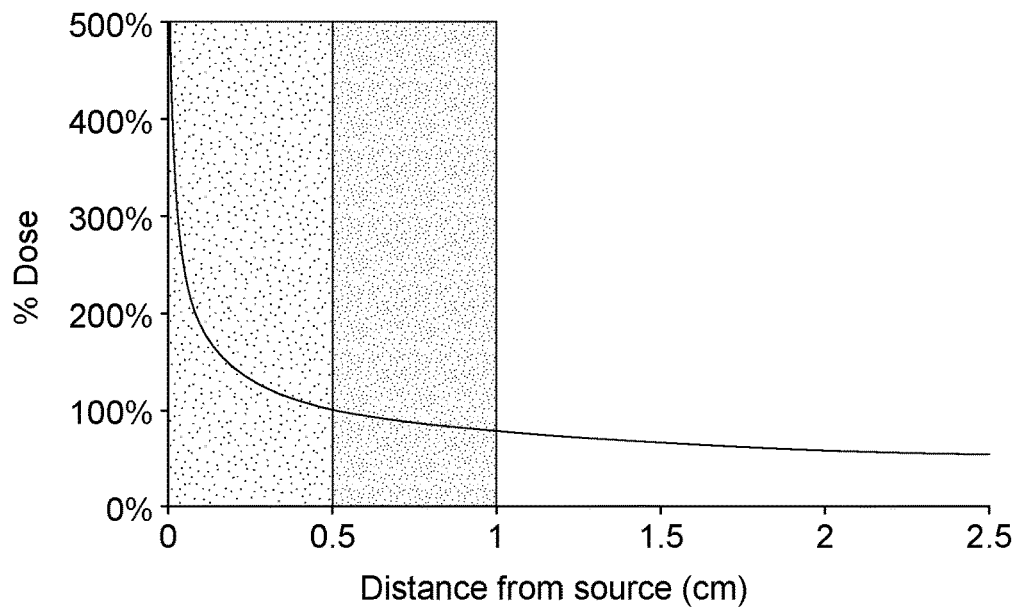
FIG. 1 depicts exponential decay of radiation dose with radial distance from typical small diameter radiation (brachytherapy) seed. Note the steep gradient adjacent to the seed where dose falls from >500% prescribed dose at the seed surface to 100% at 5 mm distance (80% reduction). Over the next 5 mm (from 5 to 10 mm distance from seed), the dose falls off more gradually from 100% to 80% (20% reduction). This clearly demonstrates that an annular shell of tissue located from 0-5 mm distance from a seed has much larger variation in dose than if the tissue shell is located from 5-10 mm distance from the seed.

Similarly, a major issue in radiation therapy is unacceptable toxicity from excessive dose in normal tissue. As depicted in FIG. 1, for a typical small diameter radiation seed source implanted in a tumor bed, the radiation dose adjacent to the source is over five times the minimum (100%) target dose prescribed for a 5 mm rim of tissue around the seed. As seen in the shaded region between 0 and 0.5 cm from the source, radiation dose drops off very rapidly from supratherapeutic levels near the seed. Conversely, the drop off in the second shaded region from 0.5-1 cm is much more gradual. A typical goal of therapy is to maintain all critical normal tissues less than about 140% of the prescribed target dose. Clearly that goal is not attained in the first region close to the radiation source where dose falls over 80% (from over 500 to 100%), whereas that goal is easily attained in the second region further from the source where dose falls only 20% (from 100 to 80%).

Accordingly, the embodiments herein are directed towards new devices and methods for treatment of at-risk tissue surrounding a tumor resection cavity—tissue that contains a mixture of cancerous and normal tissues. Resection cavities are necessary, for example, where the bulk of tumor can be removed from the body. Unfortunately, the surgeon is not always able to remove all tumor cells and therefore there is often a rim of about 5 mm (sometimes more) of "at-risk" tissue in this tumor margin. These removable cancers are found in the head, neck, torso, back, arms, and legs, literally anywhere a cancer can grow. For example, a patient suffering from brain cancer may have the cancerous tissue removed, leaving a resection cavity inside the skull. These removals, of course, are common in other cancer forms.

Accordingly, an embodiment of the present disclosure is directed towards a device to be implanted in the resection cavity after tumor reduction surgery that will facilitate the delivery of highly localized brachytherapy. In certain embodiments, the brachytherapy is provided simultaneously with mild heating of the surrounding at-risk tissue in order to enhance radiation response locally and reduce surrounding normal tissue complications. The product will consist of a biocompatible tissue implant (e.g., a polymer slab, shell, or balloon, with approximately spherical, planar, or custom shape), which fills the resection cavity. Optimal materials for the tumor bed implant will depend on surgical site. For application in areas of the body where the surgical excision results in distinct cavities (e.g., brain, lung, breast, torso, throat, etc.) the implant may be formed of a soft biocompatible polymer implant. The shape may be pre-formed by the manufacturer to fit a preplanned shape, or it may be custom fit to the resection cavity in the operating room by injecting a polymer that is a thick viscous liquid initially at room temperature and solidifies into the precise shape of the tumor bed upon exposure to elevated body temperature (34-37° C.) and/or cure time, or a combination thereof.

When radiation seed strings are used, they often consist of high activity long half-life sources that are afterloaded into indwelling catheters for a calculated period of time to deliver the required radiation dose to tissue around the implant, and then removed after being in place for several minutes, hours or days. In some protocols, the catheter array may be left in place for multiple fractionated brachytherapy treatments, or the catheters replaced multiple times to deliver the total radiation dose. Alternatively, lower activity radiation seeds with short half-life (e.g. Cs-131 with half-life<10 days) may be implanted surgically and left permanently in the tissue without catheters to deliver the desired total radiation dose over a longer time period. In the case of Cs-131, dose is delivered slowly over a period of about 40 days before the sources decay to <5% initial radioactivity level. One advantage of permanent seed implants is that the seeds may be surgically placed in tumor and the wound closed under anesthesia, thus eliminating the inconvenience and pain of percutaneous catheters. Since the radiation dose is delivered continuously over the next 40-50 days while the patient is at home, there is no need to return for fractionated brachytherapy treatments. This permanent implant approach may have substantial advantages in overall cost of therapy as the hospital stay and number of patient visits is minimized compared to temporary implant approaches. Despite these advantages, several challenges limit more widespread use of permanent seed implants. First, the radioactive seeds can migrate to unintended locations over the >50 days of radiation dose delivery, thus exposing healthy tissues to radiation. Second, tissues close to the small diameter seeds get extremely high radiation dose in order to obtain sufficiently high minimum dose throughout the tissue target, as demonstrated in FIG. 1. If seeds are placed or migrate to locations nearby critical normal tissue structures (e.g., blood vessels or nerves), the resulting dose heterogeneity can lead to severe complications.

Figure 2:
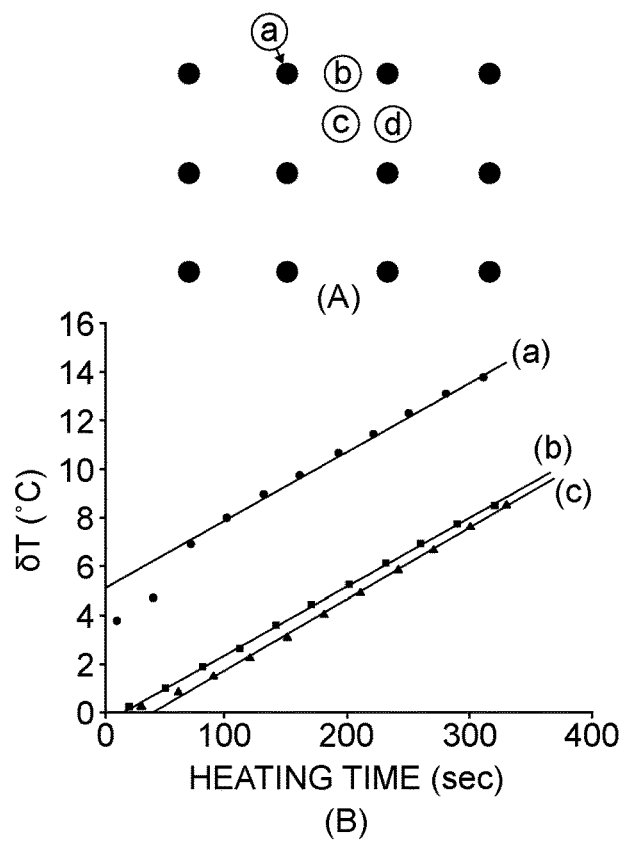
FIG. 2 depicts the prior art: (A) Cross sectional view of a previous technology ferroseed interstitial implant array defining geometry and temperature measurement locations within a 12 needle array intended for heating a solid mass tumor. (B) Typical temperature rise versus time at locations marked a, b, and c within the array of twelve ferromagnetic #430 stainless steel needles that are 1.5 mm diameter and 10 cm long in a muscle tissue equivalent phantom immersed in a magnetic field of $H_o$=420 A/m. From Stauffer et. al. (45). The temperature of tissue adjacent to the seeds (Ta) is excessively hot, whereas tissue temperatures at locations between seeds (Tb and Tc) are potentially too cool.

A further complication is related to uniformly heating a tissue target at depth in the body. FIG. 2 depicts a prior art method of producing localized heat within a deep tissue volume. The figure depicts a cross section through the center of an implant array of 12 stainless steel needles (or alternatively 12 strings of ferromagnetic seeds), each 10 cm long×1.5 mm diameter and implanted 1.5 cm apart in muscle tissue-equivalent phantom. Temperatures recorded at points a (seed surface), b (midway between two seeds), and c (midway between 4 seeds) during a 6 min application of external magnetic field at 100 kHz are depicted in the accompanying graph. As is evident, the temperature rise at point a near the heated seed produces a very hot temperature in a short amount of time, that may burn or be supratherapeutic. By comparison, the temperature rise at points b, b, and c far from the seeds is reduced nearly 6° C. from the temperature at point a, and may not reach therapeutic levels between seeds when the limit of temperature is achieved near the seeds. This severely reduces the quality of heat treatment as essentially only a limited amount of the tissue target located between points a, b and c is therapeutic, whereas remaining tissues are either damaged by excessive heat, or do not receive sufficient heat. Accordingly, new therapeutic strategies to heat tissue more uniformly are necessary to combine heat with the radiation, immunotherapy, and chemotherapy multimodality treatments disclosed herein.

Figure 3A:
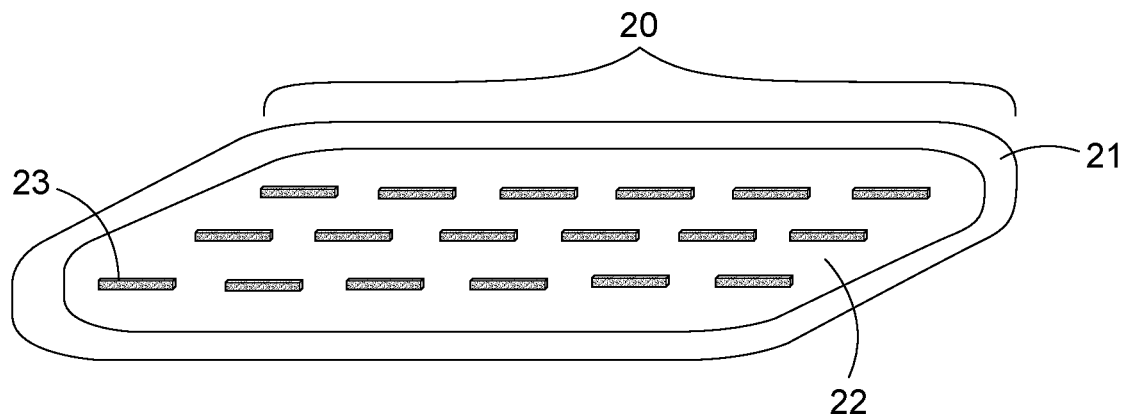
FIGS. 3A-B depict a resorbable (or alternatively a non-resorbable) polymer slab implant with radiation (RT) seeds embedded 3-10 mm deep below the surface to improve the uniformity of radiation dose delivered by the seeds to at-risk tissue around the resection cavity wall. This biocompatible brachytherapy tumor bed implant should maintain its structure for >50 days to ensure safe delivery of radiation dose and subsequently resorb in tissue within approximately 100 days (for the Cs-131 seeds in resorbable polymer example). To maintain tissue geometry permanently after surgery, a non-resorbable polymer may be used instead.

In a first embodiment, FIG. 3A depicts a biocompatible polymer slab brachytherapy tumor bed implant 20 having a polymer coating (spacer) 21 coating a polymer core 22. Within the polymer core 22 are depicted three parallel lines (strands) of evenly spaced radiation therapy seeds 23 embedded just under the surface or lying on top of the surface of the polymer core 22. The radiation therapy seeds are preferably spaced 3-10 mm from the at-risk tissue target surrounding a resection cavity wall by a polymer coating 21 layer.

The polymer coating 21 is comprised of either a resorbable or a non-resorbable biocompatible polymer material. A non-resorbable polymer would be utilized in instances where the resection cavity should be filled and maintained equal volume after surgery, so as to prevent a cavity in the skin for example. Conversely, a resorbable polymer can be advantageously utilized where the resection cavity should collapse back to its size before the growth of the tumor cells that are excised. The polymer core 22 is similarly made of either non-resorbable or resorbable polymer. In certain embodiments, the same polymer can be utilized for both the polymer coating 21 and polymer core 22, though different polymers or densities can be utilized as necessary for the particular application.

Figure 3B:
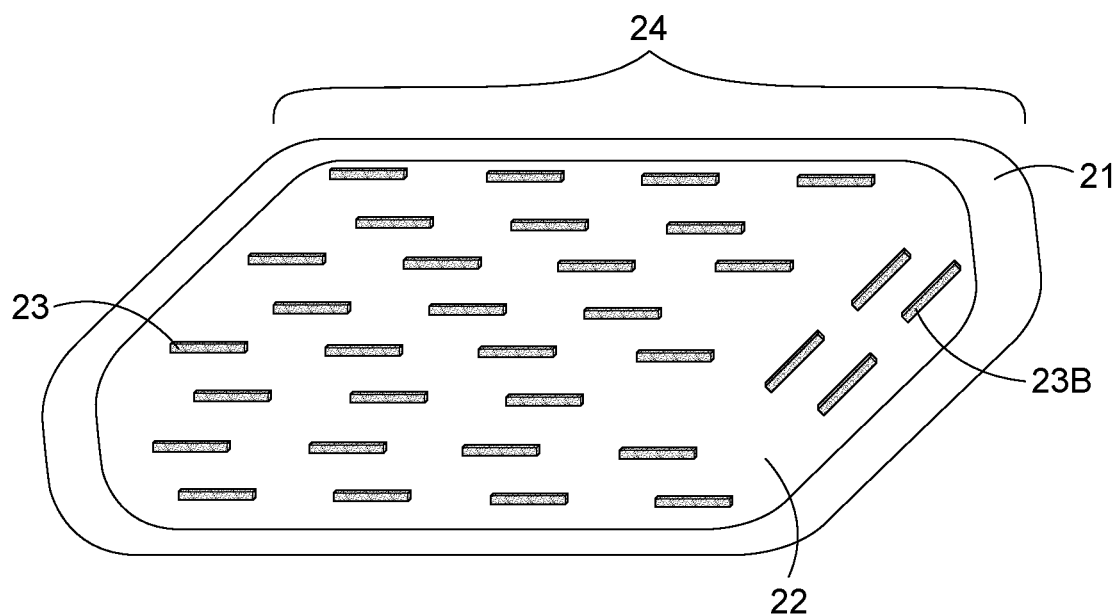

FIG. 3B depicts a variation of FIG. 3A, wherein a polymer slab implant 24 comprises radiation therapy seeds 23 placed in multiple mostly parallel seed strands, as well as seeds 23B oriented at angles to the parallel seed strands, as necessary to provide the most evenly spaced location of seeds all around the periphery of an irregularly shaped resection cavity wall. Appropriate numbers of parallel seeds 23 and angled seeds 23B, in multiple strands, are embedded in the polymer core 22 to ensure uniform spacing all around the polymer core 22. The polymer coating layer 21 provides a uniform 3-10 mm thick separation of radiation and ferroseeds from the resection cavity wall.

Indeed, another preferred embodiment of this tumor bed shaped implant will add ferromagnetic seeds interspersed between the radiation seeds and distributed uniformly around or under the surface of the polymer implant. In one form, these ferroseeds 26 will be similar in size and interspersed alternately with radiation seeds 23 along each seed string (e.g. FIG. 4A). The ferroseeds 26 may be heated to the desired treatment temperature one or more times after surgery by placing the patient inside a non-contacting induction coil and applying an external magnetic field that couples electromagnetic energy into the ferroseeds to make them hot. To facilitate delivery of appropriate temperatures that enhance the radiation effect, the seeds may be fabricated from an alloy having an appropriate Curie point temperature such that the seeds effectively self-regulate at the desired treatment temperature, normally around 45-50° C., though that temperature could range as high as 100° C. for thermal ablation applications.(44, 74-77)

For many clinical applications, the tumor bed implant will be fabricated from biocompatible resorbable polymer material that resorbs into tissue only after the delivery of radiation dose is complete. As the polymer material is resorbed, the implant region is debulked and the strings of now inactivated radiation seeds 23 and/or interspersed ferroseeds 26 are left in a fibrosed tissue, thereby limiting seed movement in the years thereafter. For some clinical applications, a formulation of polymer that does not resorb over time is preferred. This permanent implant would maintain the structure of the resection cavity long after surgery and ensure no migration of the seeds.

Advantages from use of the proposed multimodality polymer implant include the ability to close the surgical wound at the time of tumor resection leaving a permanently implanted tumor bed shaped implant that will deliver appropriate radiation and heat doses (and potentially chemotherapy and/or immunotherapy drug infusions) with no externalized connections. The patient can go home soon after surgery with no needles or catheters penetrating the skin. Low energy sources, such as Cs-131 are safe for the family with minimal precautions. The radiation dose distribution is significantly more uniform throughout the at-risk tissue surrounding the resection cavity due to the 3-10 mm separation of radiation seeds from tissue provided by the intervening polymer. In the case of radiation fluid uniformly mixed into the polymer in place of individual radiation seeds, the radiation dosimetry is even more uniform around the surface of the implant. Similarly, the thermal dose from embedded ferromagnetic seeds is significantly more uniform than from standard interstitial heating technology due to the 3-10 mm spacing of seeds from the target tissue. And like the radiation dose, the uniformity of thermal dose may be maximized using magnetic nanoparticles distributed uniformly within the polymer. Heat treatments can be accomplished with no external connections to the power source as heat is coupled inductively to the seeds from the external magnetic field; no invasive connections are required. The radiation dose is delivered slowly over approximately 50 days post implant, allowing higher overall dose with less normal tissue complications than a single radiation dose at the time of surgery or several short radiation doses closely spaced in time soon after surgery. The improved homogeneity and extended duration of radiation dose delivery should reduce the risk of severe radiation-related side effects, which include: carotid artery rupture, osteo- or condro-radionecrosis, wound healing complications, fistula formation, cranial nerve damage, or skin and subcutaneous tissue necrosis among others. Moreover, the synergistic effect of combining heat treatment with radiation should significantly improve overall response with minimal impact on normal tissue toxicity (57, 58).

Options for heating tissue around the implant are considered and the feasibility established for heating the entire tumor bed with an externally applied magnetic field in the range of about 50-500 kHz that couples energy into small magnetic particles distributed throughout the implant. Theoretical estimations of potential ferromagnetic seed heating at depth in tissue have been confirmed with laboratory experiments of ferromagnetic seed heating at 100 kHz (45, 48) with one example of prior art tissue heating implant shown in FIG. 2. Subsequent clinical use of ferromagnetic seed implant arrays has confirmed the ability to couple heat inductively into parallel catheter implant configurations of ferromagnetic seeds (72, 78) and magnetic nanoparticles (49, 50, 61, 62) implanted in deep seated tumors. The thermal dosimetry of these interstitial seed array implants (54) clearly demonstrates the theoretical advantage of the proposed polymer implants that provide physical separation between the hot ferromagnetic seeds and target tissue. We describe a new and unique approach for treatment of tumor bed tissues surrounding resection cavity implants, including those in the head and neck, brain, lung, breast, liver, colon, and other organs where such therapeutic treatment will be suitable and more effective than prior technology.

Figure 4A:
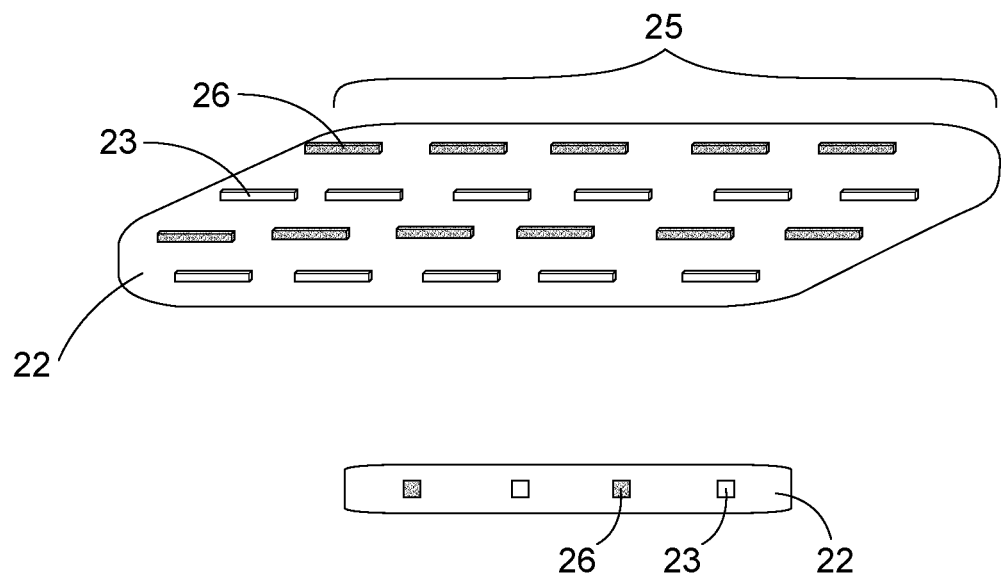
FIGS. 4A-B depict a resorbable (or alternatively a non-resorbable) polymer implant with radiation seeds and ferromagnetic (HT) seeds interspersed and embedded 3-10 mm deep below the surface to improve the uniformity of radiation and thermal doses delivered to at-risk tissue around the resection cavity wall. This biocompatible thermobrachytherapy tumor bed implant should maintain its structure for >50 days to ensure safe delivery of radiation dose with adjuvant heat and subsequently resorb in tissue within approximately 100 days (for the Cs-131 seeds in resorbable polymer example). To maintain tissue geometry permanently after surgery, a non-resorbable polymer may be used instead.
Figure 4B:
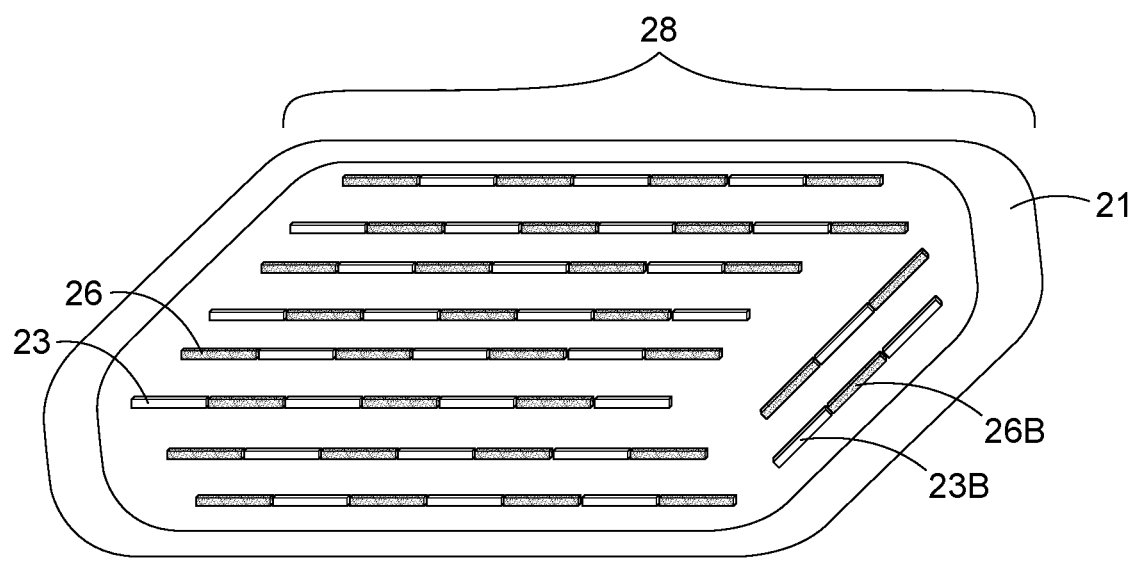

FIG. 4A depicts a further embodiment of a thermobrachytherapy slab 25, comprising a polymer core 22, regularly spaced radiotherapy seeds 23 and heat therapy seeds 26. A side view is provided in FIG. 4A so as to provide for appropriate visualization of the required spacing between the seeds and edge of overlying polymer. A further polymer coating may be included, as is depicted in FIG. 4B. The seeds are spaced at a regular and consistent spacing to ensure consistent and even therapeutic doses to adjacent cells.

FIG. 4B provides a further embodiment of a thermobrachytherapy implant 28, having multiple mostly parallel seed strands 23 embedded in the polymer core 22 as well as seeds 23B at angles to the parallel seed strands 23, as necessary to provide the most evenly spaced location of seeds all around the periphery of the polymer core even in irregularly shaped resection cavity. Appropriate numbers of parallel seeds 23 and angled seeds 23B, in multiple strands, are embedded in the polymer core 22 to ensure uniform spacing all around the polymer core 22. The implant further comprises a polymer coating layer 21 that provides a uniform 3-10 mm thick separation of radiation and ferroseeds from the resection cavity wall.

One preferred embodiment of the invention involves formation of a biocompatible resorbable implant inside the surgical cavity that can be fitted with a mesh of equally spaced radioactive seeds that deliver 95% of their radiation dose over a period of about 40 days, with dose rate continuing to fall off slowly thereafter. In addition, this implant would incorporate an array of equally spaced ferromagnetic seeds that can be coupled to an external magnetic field for delivery of heat treatments to enhance the radiation effect, for example FIGS. 4A and 4B. Heat treatments can be performed 1-7 times a week, for a duration of between 1 minute and 24 hours, inclusive of all times within. Preferably, treatment is 1-2 times a week for a treatment time between 30 minutes and 1 hour. For tumor sites that will benefit from decompression of the tissue following treatment, the tumor bed implant will resorb slowly over months following delivery of the thermoradiotherapy dose, thereby debulking the site and leaving the inactivated biocompatible seeds permanently immobile in the remaining fibrotic scar. In certain embodiments, each of the polymer core 22 and coating 21 may absorb or be non-absorbable as necessary for the clinical indication.

Figure 5A:
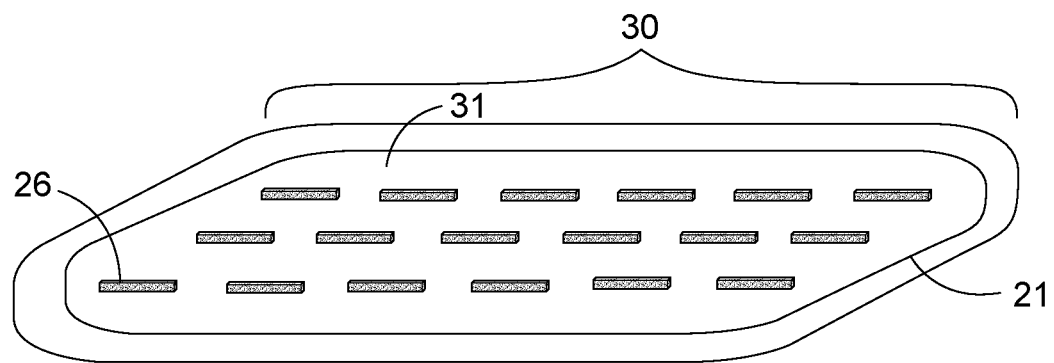
FIGS. 5A-B depict a resorbable (or alternatively a non-resorbable) polymer implant with ferroseeds uniformly spaced around the periphery and embedded 3-10 mm deep below the surface to improve the uniformity of radiation and thermal doses delivered to at-risk tissues around the resection cavity wall, with a chemotherapeutic and/or immunotherapy agent impregnated within the polymer. The polymer may be configured to break down rapidly when the ferroseeds are heated and release therapeutics into the heated tissue around the resection cavity quickly during the heat treatment. Alternatively the polymer may be formulated to resorb slowly over time and release therapeutics slowly over a period of time with 1-10 heat treatments to enhance the delivery and local activity of the therapeutics. The implant may optionally contain radiation therapy seeds interspersed uniformly around the ferroseeds, to accomplish thermobrachy/chemo/immunotherapy. That biocompatible multimodality tumor bed implant configuration should maintain its structure for >50 days to ensure safe delivery of radiation dose with adjuvant heat and subsequently resorb into the surrounding tissue in approximately 100 days while slowly releasing the chemotherapy and/or immunotherapy agents.

FIG. 5A provides a further embodiment, comprising a biocompatible polymer thermo/chemo/immunotherapy implant 30 that comprises ferroseeds 26 within the polymer core 31. This embodiment provides the opportunity to include chemotherapeutic and immunotherapy agents mixed within the polymer structure which will be delivered slowly into the target tissue around the implant as the polymer material is resorbed. The chemo or immunotherapeutic materials can be impregnated within either the polymer coating 21 or polymer core 31 material, or in both the spacer 21 and core 31. The implant 30 may optionally comprise radiation therapy seeds, as provided in prior embodiments, to accomplish multimodality treatment with thermobrachy/chemo/immunotherapy. In embodiments wherein the radiation therapy seeds are utilized, this slow release of drug will normally occur after a delay from the end of thermobrachytherapy treatment, and, thus, will provide appropriate separation of toxicities from the radiation and chemotherapy doses while adding therapeutic benefit from both treatments from the same multimodality tumor bed implant.

Figure 5B:
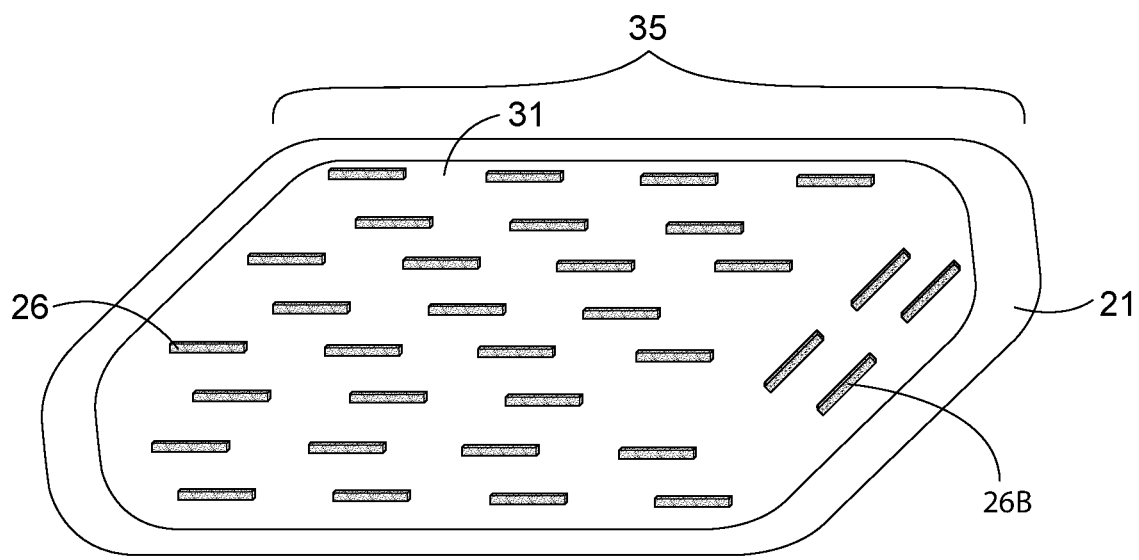

FIG. 5B depicts a variation of FIG. 5A wherein the polymer slab implant 35 comprises ferroseeds 26 placed in multiple mostly parallel seed strands, as well as seeds 26B oriented at angles to the parallel seed strands, as necessary to provide the most uniformly spaced location of thermal seeds all around the periphery of the polymer core 31, even in an irregularly shaped resection cavity. The polymer coating layer 21 provides a uniform 3-10 mm thick separation of ferroseeds from the resection cavity wall. This embodiment provides the opportunity to include chemotherapeutic and immunotherapy agents mixed within the polymer structure which will be delivered slowly into the target tissue around the implant as the polymer material is resorbed. The implant 35 may optionally comprise radiation therapy seeds, as provided in prior embodiments, to accomplish multimodality treatment with thermobrachy/chemo/immunotherapy. In embodiments wherein the radiation therapy seeds are utilized, this slow release of drug occurring after a delay from the end of thermobrachytherapy treatment should provide appropriate separation of toxicities from the radiation and chemotherapy doses while adding therapeutic benefit from both treatments from the same multimodality tumor bed implant.

Figure 6:
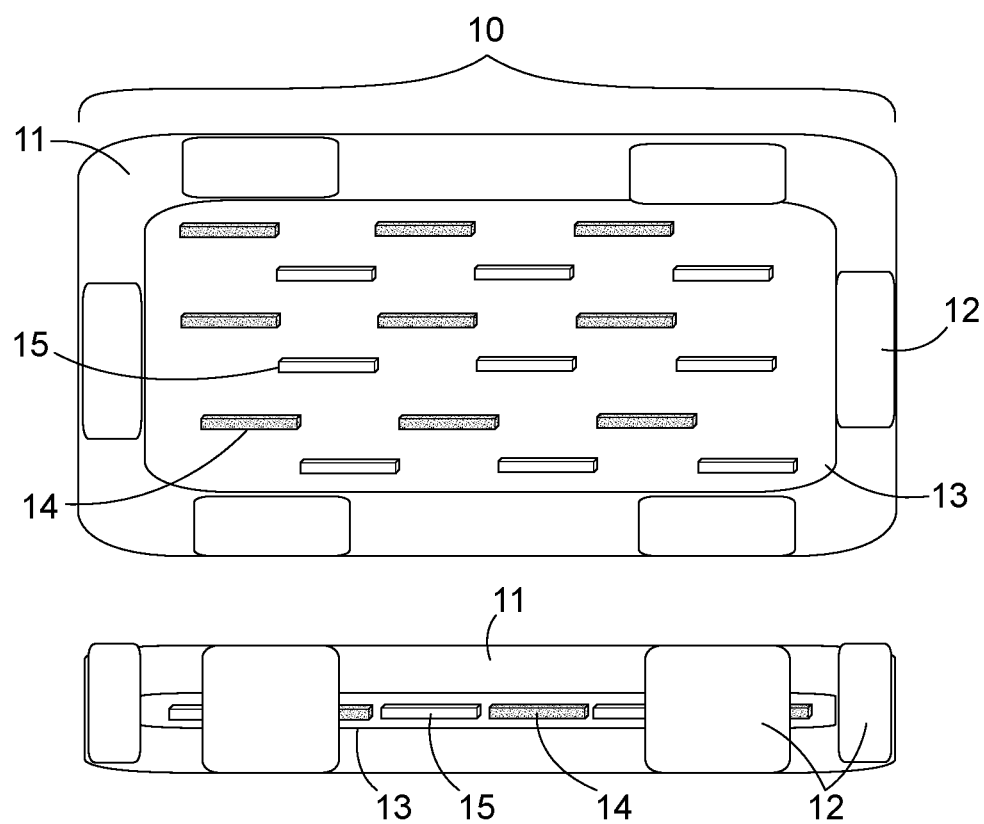
FIG. 6 depicts a resection cavity implant with resorbable polymer core having strings of radiation seeds interspersed with ferroseeds uniformly spaced around the surface. This seed-wrapped polymer core is inserted into the resection cavity with polymer spacers to maintain the desired separation of seeds from surrounding tissue while an ungelled viscous liquid polymer is injected into the cavity to make a 3-10 mm thick coating of polymer around the core. The polymer gel becomes solid in minutes at body core temperature, which then maintains appropriate 3-10 mm spacing of the radiation and/or ferroseeds from the resection cavity wall and tumor margin.

FIG. 6 depicts a further embodiment of a polymer slab implant 10, comprising an inner preformed polymer core 13, spacers 12 positioned around the preformed polymer core 13, and a resorbable polymer 11 injected into the cavity to fill the space between the inner preformed core 13 and the edge of the resection cavity. Positioned within the inner preformed core 13 are seed strings. The seed strings include ferroseed strings 14, which are uniformly spaced around the periphery of the preformed core 13 as well as radiation therapy seed strings 15, also uniformly spaced around the periphery of the preformed core 13. Alternatively, individual ferroseeds 14 and radiation seeds 15 may be interspersed uniformly around the periphery of the core 13. In certain embodiments, Cs-131 is the preferred radiation source, due to its half-life properties, allowing for the material to stay in the body while delivering the radiation dose over about 50 days. The resorbable polymer 11 also fills around the spacers 12 to make a uniform thickness layer of polymer overlying the radiation seeds 15 and ferroseeds 14 in the inner core 13.

Figure 7:
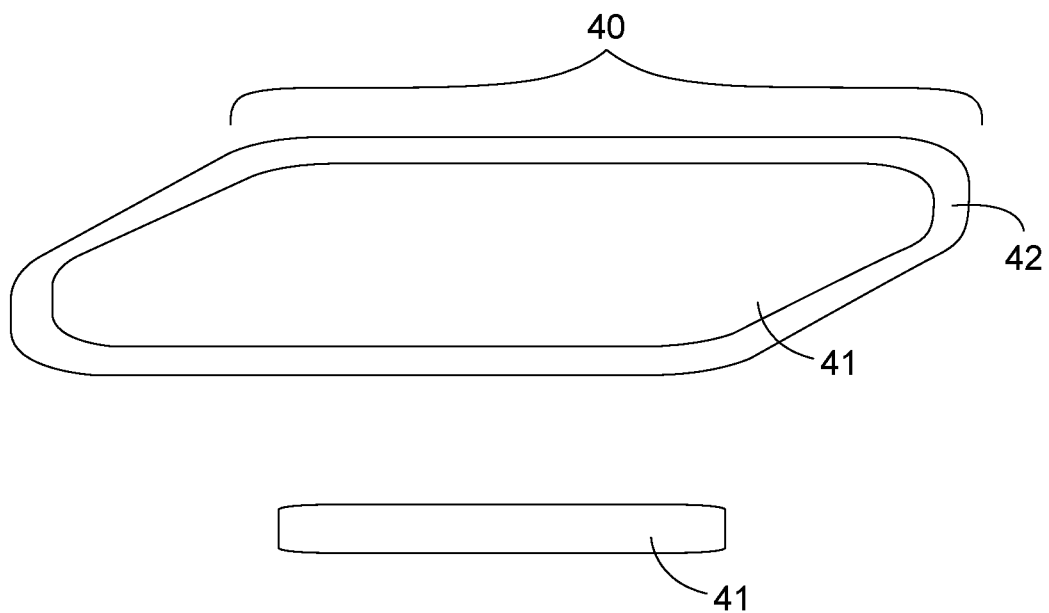
FIG. 7 depicts a biocompatible resorbable polymer implant with magnetic nanoparticles and chemotherapeutic and/or immunotherapy agents uniformly mixed throughout the polymer. This configuration allows heating of resection cavity wall with magnetic coupling to an eternal magnetic field while the region is irradiated with external beam radiation if desired. After all thermoradiation treatments are completed, the polymer resorbs slowly in time releasing the chemotherapeutics. Alternatively, the polymer could be formulated to melt at a specific temperature (e.g. 44° C.) and thus rapidly release all chemotherapeutics at the time of heating to deliver most concentrated local chemotherapy dose.

FIG. 7 depicts a variation of the thermochemotherapy implant, wherein the polymer implant 40 contains no heat or radiation therapy seeds. Instead, the slab 40 contains a polymer 41 that is uniformly impregnated with magnetic nanoparticles. These nanoparticles, like the heat seeds, can be heated with an external power source. This configuration allows combination with external beam radiation therapy provided to the region of the resection cavity, in combination with heating of surrounding tissue by thermal conduction. The polymer 41 can be optionally further impregnated with therapeutic materials, such as chemotherapeutic or immunotherapeutic materials which will be delivered slowly to the target tissue as the polymer material is resorbed. Heat treatments may be applied 1-2 times per week during this resorption period to enhance the local delivery and activation of therapeutics in at-risk tissue surrounding the resection cavity implant. FIG. 7 depicts a further polymer coating 42 surrounding the polymer 41 that can be optionally added. For example, the implant may contain only the polymer 41 or both the polymer coating 42 and the polymer 41, each of which can be modified as described herein.

Figure 8:
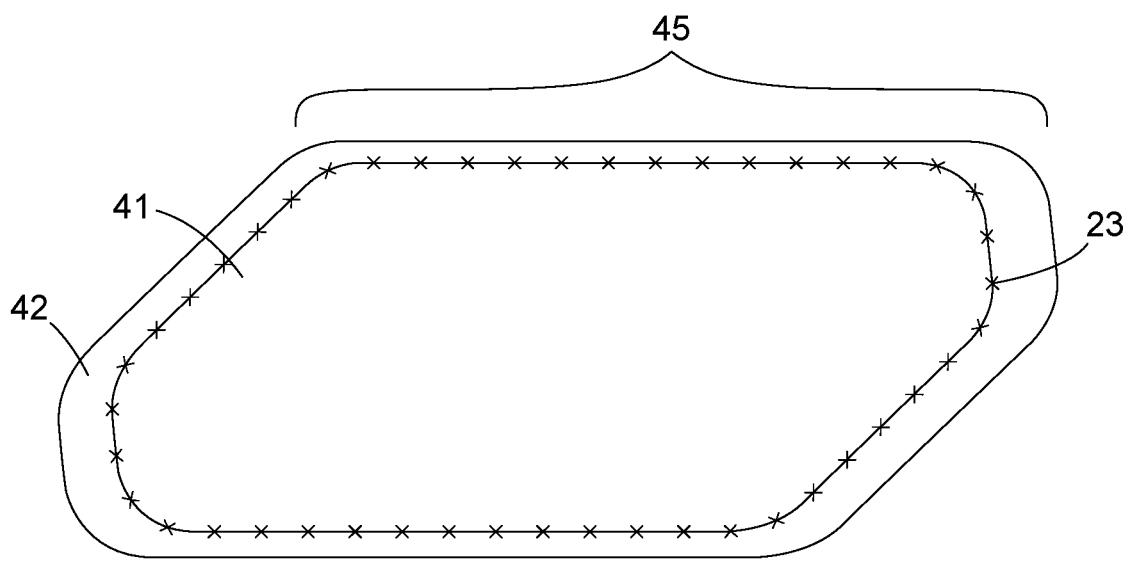
FIG. 8 depicts a biocompatible non-resorbable polymer core implant with radiation seeds (e.g. Cs-131) uniformly spaced around the periphery of the polymer core under 1-5 mm of polymer. A second layer of biocompatible resorbable polymer with magnetic nanoparticles and chemotherapeutic and/or immunotherapy agents uniformly mixed throughout the polymer which covers the radiation seeds with 1-10 mm thick layer of resorbable polymer. This configuration allows heating of resection cavity wall 1-10 times with magnetic coupling to an external magnetic field during the 50 day delivery of brachytherapy. After brachytherapy is complete, the outer layer of resorbable polymer resorbs slowly in time releasing the chemotherapeutics and allowing the body to dissipate and eliminate the magnetic nanoparticles from the body.

FIG. 8 depicts a biocompatible non-resorbable multilayer polymer implant 45 with radiation seeds 23 uniformly spaced around the periphery of the polymer core 41. A second layer of biocompatible resorbable polymer coating 42 with magnetic nanoparticles and chemotherapeutic and/or immunotherapy agents uniformly mixed throughout the polymer which covers the radiation seeds with 3-10 mm thick layer of resorbable polymer. This configuration allows heating of resection cavity wall, e.g., 1-10 times with magnetic coupling to an external magnetic field during the 40-50 day delivery of brachytherapy. After brachytherapy is complete, the outer layer of resorbable polymer 42 resorbs slowly in time releasing the chemotherapeutics. Heat treatments may continue 1-2 times per week during the period of radiation treatments and again during the period of release of chermotherapeutics as optimum for multimodality treatment of the tissue. This configuration debulks the region around the resection cavity after the end of multimodality treatments and eliminates all magnetic material from the body, while leaving only the biocompatible polymer core 41 with embedded radiation seeds (RT) 23 when it is non-resorbable. Alternatively, the polymer core 41 with embedded RT seeds 23 may be resorbable into the body after the end of radiation treatment leaving the decayed radiation seeds in the fibrosed scar of the resection cavity.

Methods of treatment using the any of the above described devices comprises inserting the device into a resection cavity. Depending on the particular need, the device can be pre-molded, or can be molded with a suitable fluid which will harden in the cavity as a polymer core. Radiation seeds and a magnetic material are added, either in or around the polymer core. Optionally, a liquid polymer can be further injected around the polymer core to create appropriate space between the cells at the edge of the resection cavity and the radiation seeds. A magnetic force can then be applied externally to the patient to heat the magnetic material (ferroseeds or a magnetic nanoparticle).

Figure 9A:
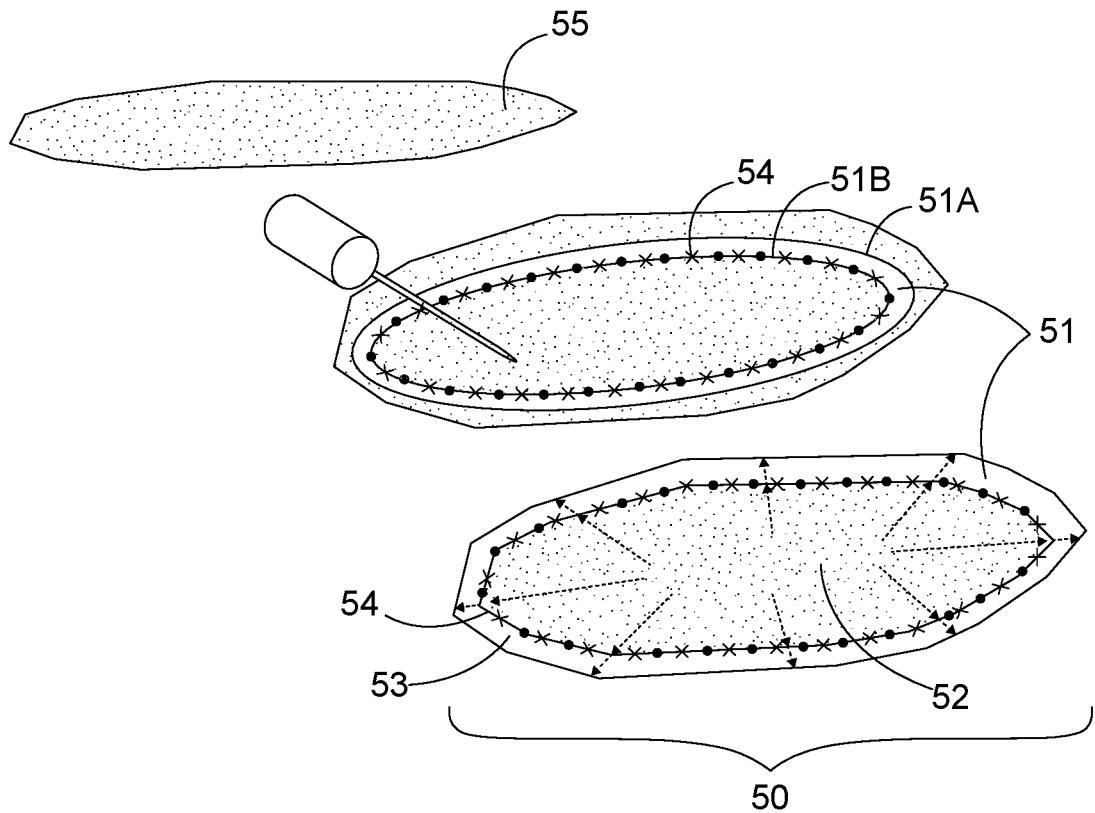
FIG. 9A depicts a biocompatible expandable thick wall polymer shell with radioactive and/or ferromagnetic materials embedded within the inner surface of the shell which is filled with saline or liquid polymer to expand to fill the resection cavity. The magnetic materials can be heated 1-10 times during the delivery of radiation by coupling to an external magnetic field. In this configuration, the biocompatible polymer shell remains in place indefinitely without resorption into the body for cosmetic or structural reasons.
Figure 9B:
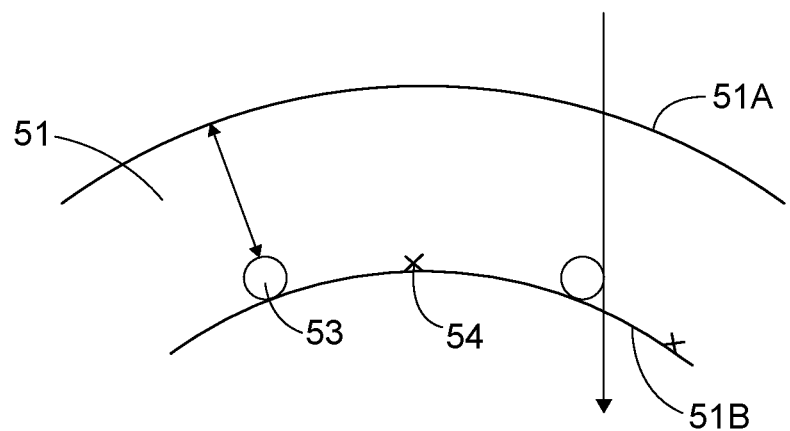
FIG. 9B magnifies a section of the polymer shell wall showing the seeds embedded such that there is a 3-7 mm thick layer of polymer separating the seeds from the resection cavity wall tissues.

In another preferred embodiment, as depicted in FIG. 9A depicts a resection cavity 55. The multimodality treatment device 50 comprises a biocompatible expandable hollow polymer shell 51 with uniformly spaced radiation seeds 53 and ferromagnetic seeds 54 embedded in the inner surface 51B of the thick wall polymer shell 51 for thermobrachytherapy over approximately fifty (50) days interspersed with hyperthermia treatments 1-2 times weekly. The hollow polymer shell 51 is expandable, like a balloon, and thus can be filled with a liquid polymer, saline, or other suitable material. The liquid polymer core 52 can also be filled and itself would expand the polymer shell 51 outwards. This forces the outer wall 51A against the resection cavity 55. A detail cross-section of the polymer shell 51 is depicted in FIG. 9B. In a preferred embodiment, the hollow core 52 is filled with liquid polymer to expand the polymer shell 51 to fill the resection cavity 55 with the outer surface 51B contacting the cells at the resection cavity wall. The 3-8 mm thick wall of polymer shell 51 provides the correct separation distance of radiation seeds 53 and ferroseeds 54 from tissue around the resection cavity wall.

Figure 10:
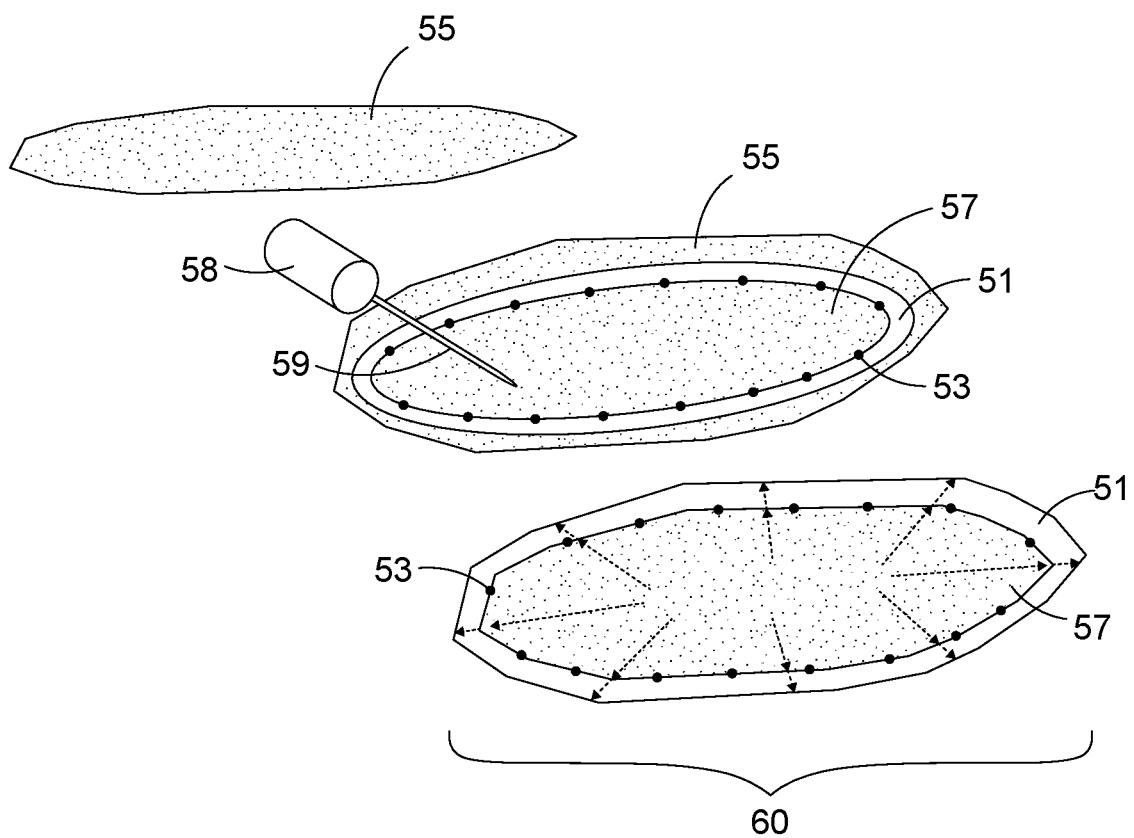
FIG. 10 depicts a biocompatible expandable thick wall polymer shell with radioactive seeds embedded within the inner surface of the 3-7 mm thick shell. In this configuration, the shell is filled with magnetic nanoparticles (or magnetic fluid), or a homogenous mixture of radiation fluid (e.g. Iotrex, Cesitrex) and magnetic nanoparticle fluid. The magnetic nanoparticles can be heated 1-10 times during the delivery of radiation by coupling to an external magnetic field. A resorbable or non-resorbable polymer may be used depending on clinical application.

In an alternative configuration depicted in FIG. 10, the device 60 would consist of a biocompatible expandable hollow polymer shell 51 with uniformly spaced radiation seeds 53 embedded in the inner surface 51B of the thick wall polymer shell 51, as in FIG. 9B. In this configuration, the interior would be filled with magnetic heating material 57 that may consist of tightly packed small ferromagnetic spheres, particles, or magnetic nanoparticle fluid. The thick wall polymer shell 51 may be filled or partially filled prior to surgical placement, and the volume expanded to completely fill the resection cavity by injection of additional fluid via needle (or catheter) 59 and syringe 58. The polymer shell 51 may be formulated from non-resorbable or resorbable material to fit the clinical application. Alternatively, the magnetic heating material may be mixed and distributed within the polymer shell 51, and the inner core 57 filled with a non-magnetic fluid or polymer. When magnetic nanoparticles are used in a resorbable polymer implant, the small nanoparticles may dissipate from the region and be excreted from the body as the polymer shell is resorbed in tissue whereas the radiation seeds would remain permanently fixed in the scar tissue of the collapsing resection cavity wall. Elimination of all magnetic nanoparticles from the region following treatment has the advantage of avoiding image artifacts in any future Magnetic Resonance imaging of the region. Finally, the polymer shell 51 can be filled with a magnetic material, such as a magnetic nanoparticle, and the cores 52 or 57 can be filled with a polymer. This allows the core to inexpensively expand to press outwards on the polymer shell 51 while the expensive magnetic material fills the smaller volume of the polymer shell in direct contact with the tissue target.

Accordingly, methods of treatment of cancerous cells using the device according to FIG. 9 or 10 includes resection of a tumor, application of the polymer shell into the resection cavity. The surgeon can then inject a fluid into either the core or into the polymer coating 51. The fluid, or the device itself, comprises ferroseeds or a magnetic nanoparticle which can be heated. This fluid injection will allow the polymer coating 51 to expand to contact the edge of the resection cavity. The method further comprises applying an energy source to the patient to heat the ferroseeds or magnetic nanoparticles to increase the temperature to the cells at the edge of the resection cavity.

Figure 11:
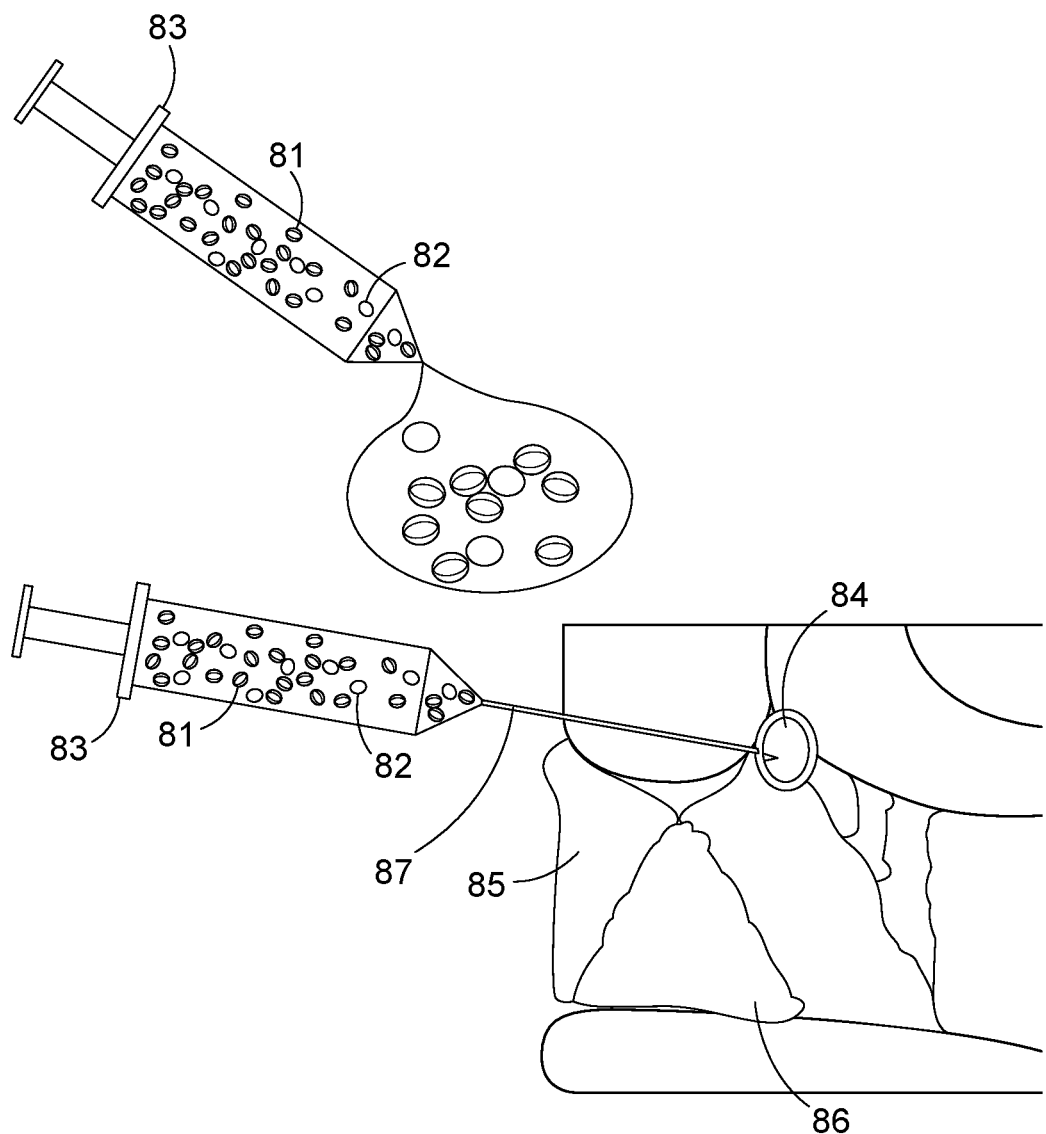
FIG. 11 depicts an alternative configuration where a viscous colloidal solution containing radioactive particles and/or magnetic particles are injected directly into the tumor resection cavity, or delivered into the interior of an expandable tumor cavity fitting shell using a needle or catheter as depicted in FIG. 10. The viscous liquid polymer may become solid shortly after delivery into a tumor resection cavity due to higher body temperature or time cure. Of all implant configurations, this colloidal solution of intermixed radiation and/or magnetic particles filling the tumor bed should provide the most uniform heat and radiation dosimetry all around the resection cavity wall, even for irregular shape cavities.

FIG. 11 depicts an alternative configuration of polymer implant consisting of viscous colloidal solution containing radioactive material 81 mixed homogeneously with magnetic particles 82 that can be injected through, for example a syringe 83, and into the body through a needle or catheter 87 directly into a tumor resection cavity 84 or delivered into the interior of an expandable tumor cavity fitting polymer shell 51 as in FIG. 10. The viscous liquid polymer may be formulated as one or two component mixture that becomes solid shortly after delivery into the tumor resection cavity due to higher body temperature or time cure. Of all implant configurations, this colloidal solution of intermixed radiation and/or magnetic particles filling the tumor bed should provide the most uniform heat and radiation dosimetry around the resection cavity wall.

Figure 12A:
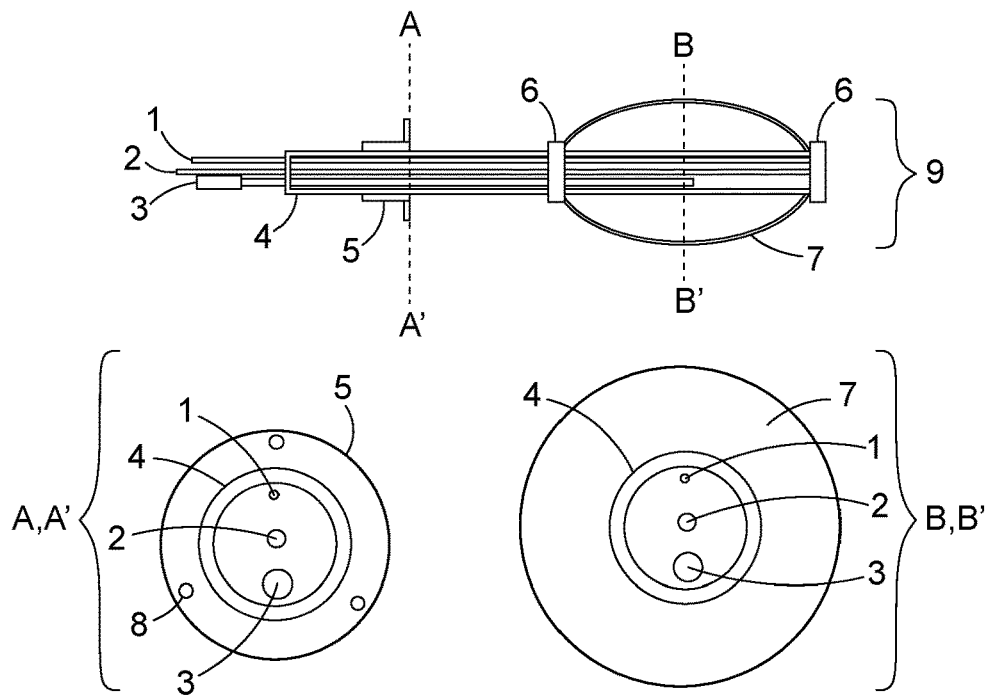
FIGS. 12A-B depict an alternative configuration where the radiation and heat sources are delivered into the tumor resection cavity via a biocompatible flexible sheath connection to a biocompatible expandable thin wall polymer (balloon). The radiation seed may be inserted into one or more central catheters that extend from outside the patient through an incision in the skin to the tip of balloon implanted in the resection cavity. Typically a High Dose Rate (HDR) afterloading device would be used to move a high activity radiation seed in precalculated steps along the one or more internal catheters to deliver most uniform radiation dose to all tissue in contact with the balloon. The interior of balloon would be inflated through another central catheter so that the balloon fills the resection cavity with magnetic nanoparticle solution for uniform heating of the surrounding tissue via coupling to an externally applied magnetic field. Temperature of the nanoparticle solution inside the balloon is monitored with a temperature sensor in another central catheter.
Figure 12B:
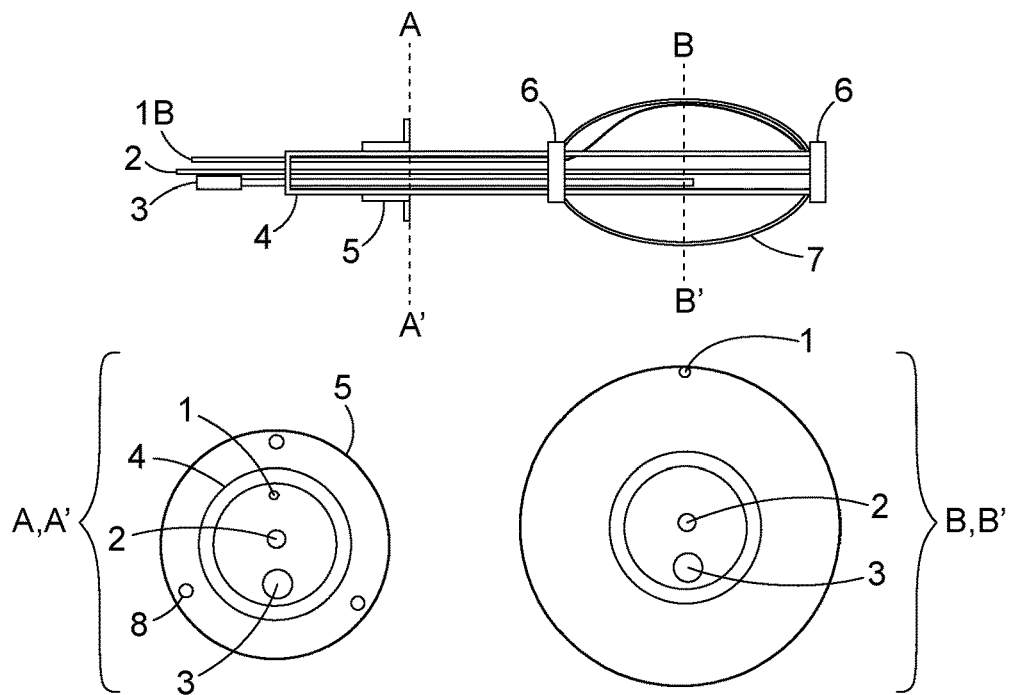

FIGS. 12A-B depict an alternative configuration where the radiation and heat sources are delivered into the tumor resection cavity via a biocompatible flexible sheath 4. A high activity radiation source may be inserted into one or more central catheters 2 that extend from outside the patient through an incision in the skin to the tip of balloon which is implanted in the resection cavity. Typically a High Dose Rate (HDR) afterloading device would be used to move the radiation source in precalculated steps along the one or more internal catheters 2, to deliver a computer planned radiation dose distribution to all tissue in contact with the balloon. The interior of balloon 7 would be inflated through another central catheter 3 so that the balloon 7 fills the resection cavity with magnetic nanoparticle solution for uniform heating of the surrounding tissue via coupling to an externally applied magnetic field. Temperature of the nanoparticle solution inside the balloon is monitored with a temperature sensor in another central catheter 1. FIG. 12B provides similar heat and radiation to the resection cavity wall with the addition of a temperature sensor that can be pulled along a catheter 1B that extends just inside the outer balloon wall and along the flexible sheath. Both configurations include a biocompatible polymer collar 5 with suture holes 8 to anchor the collar to the tissue surface and thereby secure the flexible shaft 4 to the skin.

Figure 13:
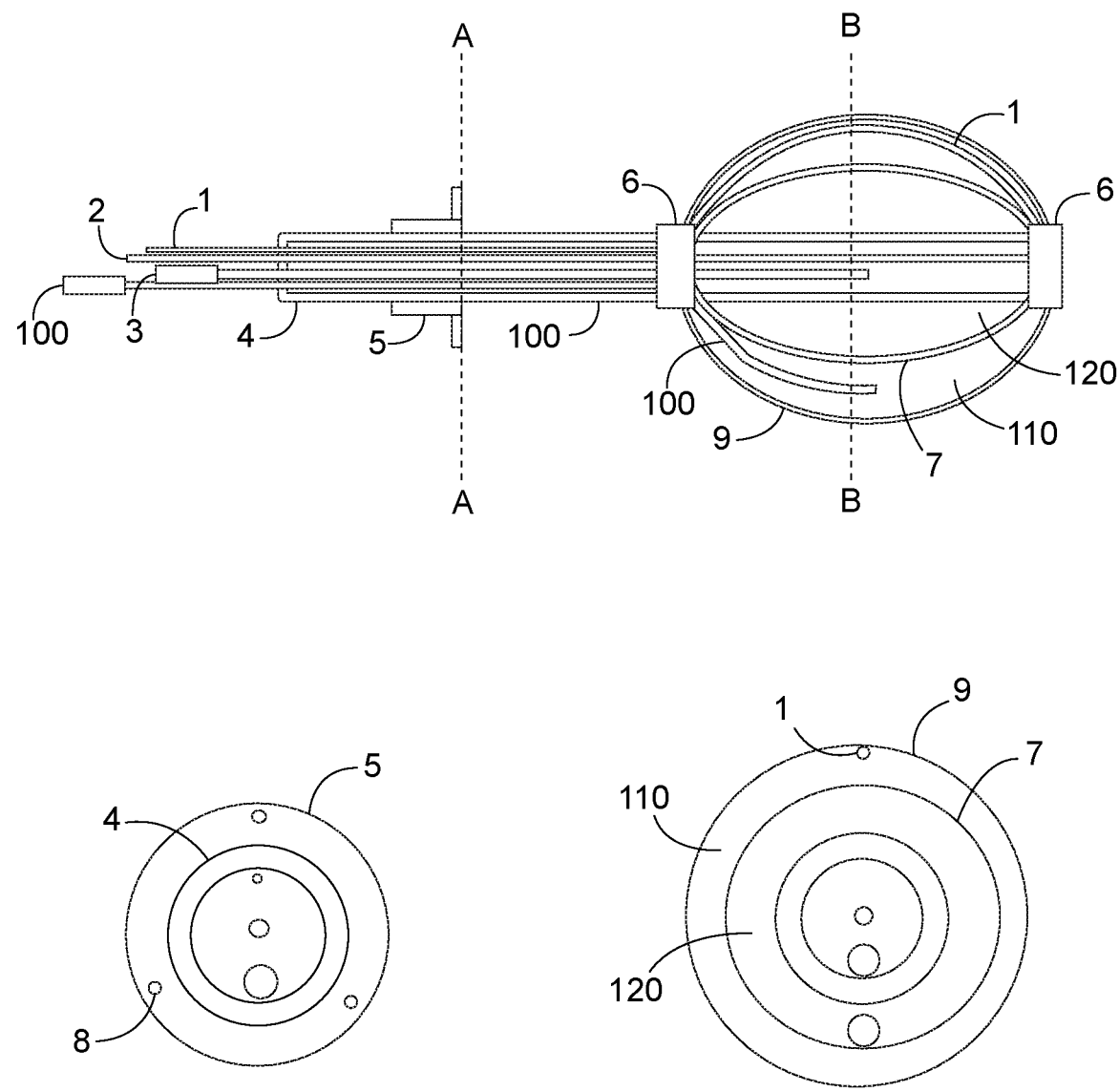
FIG. 13 depicts an alternative configuration of the biocompatible balloon design of FIG. 12 with two concentric thin wall balloons connected via biocompatible flexible sheath. The outer balloon may be filled through an external port with homogeneous mixture of magnetic nanoparticles and radiation fluid while the inner balloon is inflated with sterile saline to expand the balloon to fill the tumor resection cavity. The magnetic nanoparticles can be heated 1-10 times during the delivery of radiation by coupling to an external magnetic field while temperatures of the outer balloon surface are measured with a temperature probe pulled in a catheter contacting the outer balloon wall.

FIG. 13 depicts an alternative configuration of the biocompatible balloon 7 of FIG. 12 with two concentric thin wall balloons connecting to surface ports through a biocompatible flexible sheath 4. Both expandable thin wall polymer balloons are sealed to the flexible sheath 4 at the tip and distal ends with fixation collars 6. The outer balloon 9 may be filled through an external port and catheter 100 with homogeneous mixture of magnetic nanoparticles and radiation fluid 110 while the inner balloon 7 is filled through an external port and catheter 3 with sterile saline 120 to expand the balloon to fill the tumor resection cavity. Typically a High Dose Rate (HDR) afterloading device would be used to move the radiation source in precalculated steps along the one or more internal catheters 2 to deliver most uniform radiation dose to all tissue in contact with the balloon. The magnetic nanoparticles can be heated 1-10 times during the delivery of radiation by coupling to an external magnetic field while temperatures of the outer balloon surface are measured with a temperature probe pulled in a catheter 1 contacting the outer balloon wall. A biocompatible polymer collar 5 anchors the flexible shaft 4 to the skin using sutures through suture holes 8.

The above materials can therefore be suitably utilized in a human patient, for treatment of cells surrounding a tumor resection cavity. In a preferred embodiment, a method of treatment of cancerous cells in a patient comprises inserting a therapeutic device as described above into a resection cavity; applying an external magnetic field to increase the temperature of magnetic materials in the device for a predetermined amount of time to reach a therapeutic heat at the cancerous cells to be treated. The external magnetic field can be applied 1-20 times over the course of a treatment period of 1-100 days, to increase efficacy of the treatment. Where a further therapeutic is provided, the therapeutic will be formulated with a release profile to allow for appropriately timed release into the surrounding tissues.

Materials, Methods, and Examples:

Components of the above therapeutic devices consist of biocompatible polymer materials meeting the specifications above, the mixing container (if delivered in two components), insertion device (syringe or polymer delivery applicator), and sterile packaging for use in the operating room. In one particular embodiment, the product incorporates a regularly spaced array of radioactive seeds such as the Cs-131 seed strings available from IsoRay Medical (Richland WA) with interspersed ferroseeds (such as those available from Best Medical International (Springfield VA) that are embedded within or on the surface of the polymer product. Other suitable arrangements include a configuration with each Cs-131 seed spaced equidistant around the inside of a hollow polymer shell. Cs-131 seeds can be replaced with other suitable radioactive isotopes for brachytherapy (e.g. I-125, Pd-103, etc.). Accessories might include separately purchased software to replace or adapt current radiation treatment planning software to calculate radiation dose distributions from tumor bed implants.

As briefly described in the product options above, there are a number of alternative configurations for the polymer implant product that will optimize multimodality treatment for different tumor sites. For tumors that will benefit from either decompression of the region following completion of thermobrachytherapy or sequentially timed treatment with thermobrachytherapy followed by slow release chemotherapy or immune stimulation, pre-formed pre-gelled resorbable polymer cores and flat tissue spacers may be manufactured in advance in various sizes and thicknesses to fill different size surgical cavities. Matching ungelled resorbable polymer material may be injected into the cavity around the pre-formed solid cores and radiation seeds at the time of surgery to cover the seeds with appropriate spacing to the resection cavity wall. For cases that will benefit from extended multimodality treatment, chemotherapeutics may be mixed within the polymer that are slowly released as the polymer is absorbed into tissue after the end of thermobrachytherapy, to spread out and separate toxicities from the radiation and drug treatments.

For tumor sites that will benefit from permanent structural support and maintenance of the pre-surgical shape of the tissue region, the tumor bed implant will consist of a biocompatible non-resorbable polymer that will permanently contain and stabilize radiation and ferroseeds left in tissue after treatment.

Alternative product configurations include flexible expandable thick wall polymer shells that have radiation seeds and interspersed ferroseeds embedded on the inner surface of the shell. Other products include thin wall inflatable balloon polymer shells with internal catheters that extend out to the tissue surface to introduce a remotely afterloaded brachytherapy source and sensors to monitor the temperature of magnetic nanoparticle solution contained within the balloon that fills the resection cavity. Another alternative configuration consists of an inflatable balloon with catheter extending outside the tissue surface to inject both radioactive fluid (e.g. Iotrex or Cesitrex) and magnetic nanoparticle solution into the interior of a thin wall balloon that fills the resection cavity. A further alternative is a polymer implant with two separate inflatable thin wall balloons with an inner balloon to contain saline or liquid polymer and a concentric outer balloon that contains magnetic material and/or radiation fluid and/or chemotherapeutics. These configurations are described in detail above and in the FIGS. 3-13.

One desirable product has the following features and options: biocompatible soft polymer implant that fits snugly inside the resection cavity after tumor reduction surgery. The implant may start as a high viscosity liquid at room temperature that solidifies at elevated (body) temperature or it may be supplied as a two component compound that solidifies quickly after mixing. In cases where the size and shape of the resection cavity can be planned in advance, a pre-manufactured solid polymer core implant may be available "in stock" that is close to the required size so can be shipped to the operating room (OR) in sterile packaging for insertion into the cavity. In some cases, that standard size implant may require customization by injecting additional liquid or highly viscous polymer into the cavity around the core where it solidifies in the exact shape of the cavity due to temperature and/or time cure. Some cases may benefit from injecting the sterilized biocompatible viscous liquid polymer directly into the resection cavity without a core.

For any of these polymer implant configurations, short half-life radioactive seeds (e.g. Cs-131, Pd-103, I-125) will be embedded at a fixed depth under the surface of the polymer uniformly spaced around the implant to maximize uniformity of radiation dose in surrounding target tissue. To enhance the effects of brachytherapy, Curie point ferromagnetic seeds or particles that thermoregulate at the desired treatment temperature will be embedded under the surface of the polymer uniformly spaced and interspersed between the radiation seeds for controlled heating of tissue around the implant via coupling to an external magnetic field 1-7 times per week during the irradiation period, and again during the slow release of chemotherapeutics from a resorbing multi-modality polymer implant.

Alternatively, the implant may consist of a hollow polymer shell with the interior filled with radioactive fluid and/or magnetic nanoparticle solution for most uniform distribution of radiation and thermal doses in the at-risk tissue around the implant. A skilled surgeon will recognize the proper implant, and understand the necessary steps to remove a tumor, thus creating a resection, insertion of the device with appropriate characteristics, and applying the magnetic force to impart heating to the tissue surrounding the implanted device.

Variations to the embodiments of the device include, but are not limited to the following options:

A polymer core that is resorbable or non-resorbable. This core can be performed or injected as a material that hardens via time or temperature cure. The core containing a plurality of evenly spaced radiation seeds and magnetic seeds. In certain embodiments, the radiation seeds and/or ferromagnetic seeds are replaced with nanoparticle solutions that include radioactive and/or magnetic properties. Preferably, the magnetic materials have a Curie point transition that provides thermoregulation at an appropriate treatment temperature. The polymer may further comprise a therapeutic or chemotherapeutic material that, especially in the resorbable polymers, is then passed into the adjacent tissues as the polymer resorbs.

The polymer core may further comprise a polymer coating. This polymer coating can be pre-formed or injected to the particular resection site, which may require certain spacers to be placed around the polymer core prior to injection of the coating layer. As with the polymer core, the polymer coating may be resorbable or non-resorbable and contain any or none of the following radiation therapy materials, heat therapy materials, therapeutic and chemotherapeutic materials. The polymer core and the polymer coating may be elastic and expand to fill a cavity, or can be flexible, but not expand, as appropriate.

When a flexible material is utilized, it can be envisioned as a single flexible shell that surrounds a core. The flexible shell can then be filled with a polymer material, radiation and heat materials, therapeutics and chemotherapeutics as in the prior examples, and then be filled to expand to fit the resection cavity.

In certain embodiments, the flexible shell itself is hollow, having an inner wall and an outer wall, and creating a core inside of the inner wall. The space between the inner and outer wall itself can be filled with a material, as is described in detail above.

Detailed examples of the embodiments are provided below:

In some cases, it may be awkward to force the inner core of a prefabricated resorbable (or non-resorbable) polymer implant to conform to the shape of a resection cavity. This may be addressed for many tumor sites by having on hand several preformed inner cores that will fit many different size resection cavities. After selecting the appropriate size core from a number of preformed cores already sterile on the OR tray, the Cs-131 seed and ferroseed strings can be wrapped rapidly around the surface. Then the core can be positioned in the center of the cavity while liquid gel polymer is injected around the core, filling the cavity completely and providing the required distance from seeds to resection cavity wall.

In many cases it will be difficult to hold the seed wrapped inner core well-centered in a resection cavity while the overcoating polymer is injected and solidifying in a uniform thickness layer around the core. Thus sterile sections of preformed "spacers" made of the same polymer material could be pre-manufactured in the desired thickness of the overcoat and inserted in the resection cavity around the seed wrapped inner core. Such spacers will hold the implant centered in the cavity with correct core-to-tissue separation distance while the outer polymer coating is injected and solidifying.

Alternatively, various size inner cores could be prefabricated with the seeds already embedded uniformly around and/or underlying the surface of the implant. This would allow the radiation dosimetry to be planned in advance of surgery. If the core does not entirely fill the cavity, a thicker outer coating layer of polymer material would be added to the seed embedded inner core to complete the tumor bed fit prior to insertion into the patient and the radiation dosimetry adjusted as necessary.

Planning the exact size of resection cavity in advance may be difficult or impossible in some cases. But due to advance imaging studies the approximate size of resection cavity will be known in advance for most cases. With appropriate preplanning, it should be possible to order the approximate size tumor bed implant in advance and customize its size in the operating room either by trimming the core or adding a thin overcoating of polymer to fit the actual resection cavity. For surgical cavities that were not fully appreciated in advance, the expandable polymer shell option may be used to provide a custom fit of the implant to the actual cavity by appropriate filling of the polymer shell interior with liquid polymer, magnetic fluid, and/or radioactive fluid.

Biocompatible resorbable polymer implant to be combined with permanent radiation seeds (Cs-131, I-125, or Pd-103) interspersed with ferromagnetic seeds (i.e. cylindrical or spherical). Configurations include:

Made by manufacturer in advance—slab of resorbable polymer material to use as the implant core—available for order in several standard sizes. Cover this with matching size slab of resorbable polymer of desired thickness (e.g. 3-10 mm) with permanent radiation seeds and ferroseeds uniformly spaced in a mesh on one surface. Surgeon will assemble appropriate tumor bed implant in the operating room by trimming a standard size core to fit the surgical cavity and mating one seed-containing layer on each side of the core (for large volume implants); see FIG. 3. In the simplest case, the surgeon will adhere one 3-10 mm thick polymer-only slab to one matching size 3-10 mm thick slab having a radiation seed and interspersed ferroseed mesh on the mating surface, and implant into the cavity, forming one plane of seeds buried in the middle of a 6-20 mm thick polymer sandwich, as shown in FIG. 5A and FIG. 6.

Made by manufacturer in advance—polymer implant available for order in several standard sizes/shapes—with permanent radiation seeds and interspersed ferromagnetic seeds embedded at constant depth below the surface and uniformly spaced around the surface: FIG. 4b and FIG. 5B.

Made by manufacturer in advance—polymer implant available in custom size ordered with 2-7 day lead time—with permanent radiation seeds and interspersed magnetic material embedded at constant depth below the surface and uniformly spaced around the surface. FIG. 4b and FIG. 5B.

Made by manufacturer in advance—polymer core available in several standard sizes to fit resection cavities—custom wrapped in the OR with strings of permanent RT seeds interspersed with ferromagnetic hyperthermia seeds to uniformly cover the surface—then overcoated with a top layer (~3-10 mm) of resorbable polymer and inserted in the tumor bed. FIG. 6.

Made by manufacturer in advance—core of the implant in several standard sizes to make a loose fit inside the resection cavity—custom wrapped in the OR with strings of permanent RT seeds interspersed with ferromagnetic hyperthermia seeds to uniformly cover the surface—then implanted in resection cavity with fixed thickness spacers of pre-formed resorbable polymer to hold the undersized core centered in the cavity, then inject viscous liquid resorbable polymer around the implant core to fill the resection cavity. See FIG. 6. The surgeon will close the wound as the polymer gels to form solid tumor bed shaped implant with radiation seeds and ferroseeds embedded at the desired 3-10 mm depth below the surface and thus uniformly spaced from the resection cavity wall by the custom shaped polymer coating.

Configurations include each of the prior options listed above, but wherein the material may exchange a resorbable material for a non-resorbable material in each of the prior embodiments. Indeed, some cases may benefit from combining a resorbable material as the outer layer of the implant to decompress the tissue region after completion of thermobrachytherapy, and a non-resorbable inner core material that will remain in the body to eliminate migration of seeds.

Further, the outer resorbable polymer layer might include a homogenized mixture of magnetic nanoparticles such that the particles dissipate and excrete from the body in weeks following completion of thermobrachytherapy—to enable post treatment MR imaging of the region without artifact from concentrated magnetic particles.

Biocompatible non-resorbable polymer implant with expandable polymer shell surrounding a hollow center that is made by the manufacturer in advance and available for order in several standard sizes. This polymer mixture is flexible and can expand in size as additional liquid is injected (via needle) into the shell interior prior to closing the surgical wound. This allows minor expansion of the polymer shell to fill the resection cavity, like inflating a balloon till it fills the cavity. Configurations include: a) uniformly spaced permanent radiation seeds (Cs-131, Pd-103, I-125) interspersed with ferromagnetic seeds embedded in the inner wall of a 3-7 mm thick expandable polymer shell around a hollow center filled with saline or liquid polymer; b) uniformly spaced permanent radiation seeds embedded in the interior wall of a 3-7 mm thick polymer shell around a hollow center filled with magnetic fluid core; and c) 3-7 mm thick expandable polymer shell around a hollow center filled with magnetic fluid intermixed with radioactive fluid. See FIGS. 9 and 10.

Biocompatible polymer supplied by manufacturer in sterilized ungelled form inside syringe for injection by the surgeon into the tumor resection cavity. This polymer would come in one of several alternative formulations: a) resorbable or non-resorbable formulation; b) polymer to include magnetic nanoparticles homogeneously mixed throughout and be injected around one or more radiation seeds or seed strings positioned uniformly within the resection cavity; c) polymer to include magnetic nanoparticles and radiation fluid homogeneously mixed for injection directly into the resection cavity; d) chemotherapeutic agent uniformly mixed with magnetic nanoparticles and/or radioactive material within resorbable polymer; e) immunotherapy agent uniformly mixed with magnetic nanoparticles and/or radioactive material and/or chemotherapeutic within a resorbable polymer; or f) any of the above formulations injected around the outside of an undersized polymer core (filler) already placed in the center of the resection cavity.

A further embodiment is directed towards a microscopic colloidal solution or nanoparticle containing radioactive and/or ferromagnetic particles for 3D printing or injection to the desired site of action around or within the tumor or resection cavity. The benefit of the injectable material is the small and uniform distribution of RT and HT materials in said material. This ensures a highly uniform distribution of materials to the ultimate site. As is depicted in FIG. 11, the material can be directly injected into a resection cavity of any size or shape, or adjacent to a partial resection and existing tumor.

Methods of use or treatment comprising the products as depicted in FIGS. 12A and 12B provide an embodiment comprising a balloon catheter device 9. The balloon catheter comprises a temperature probe catheter 1, a RT source catheter 2, a port 3 with a valve for inserting a fluid into the balloon; a flexible biocompatible sheath (or shaft) 4, a collar 5, to fix the sheath 4 to the skin, a balloon collar 6, to seal a balloon to the flexible sheath 4, a balloon 7, and suture holes 8 in the collar 5, to secure to the skin surface. The Flexible shaft 4 containing multiple catheters extending from outside the skin to a thin wall expandable polymer "balloon" implanted surgically in a tumor resection cavity. Accordingly, after inserting the device, a practitioner would utilize one catheter 3 to inflate the balloon with radiation fluid homogeneously mixed with magnetic nanoparticles to fill the resection cavity for simultaneous or sequentially applied heat and brachytherapy treatment of the resection cavity wall. Another catheter 1 would be utilized to monitor temperature in the interior of the balloon.

The central catheter 2 would allow connection of remote afterloader for insertion of high activity radiation source into the interior of the balloon and time sequenced radiation treatment of the resection cavity wall. Accordingly, a computer controlled program would control the timing of the catheter along a path to provide radiation to the interior wall cells of the resection cavity. This can be combined with inflation of the balloon 7 with homogeneously mixed magnetic nanoparticle solution to fill the resection cavity for simultaneous or sequentially applied heat with the brachytherapy treatment. The position of the temperature probe is different in FIGS. 12A and 12B, to measure the temperature of the fluid in the balloon, (12A) or the temperature at the interface of balloon and target tissue (12B).

Accordingly, there are several variations of the device that provide for a suitable cancer treatment device, that can be modified based on the particular circumstances of the cancer to be treated, the location, and other factors as known to one of ordinary skill in the art. Accordingly, these can then be further utilized in methods of treatment of cancer in a patient, wherein the device is implanted into the patient in order to provide therapy with multiple synergistic treatment modalities.

Clinical Application

The embodiments described herein are derived from advancements to certain prior methods and embodiments. As background for the development of the new treatment approach of this invention, several examples of appropriate clinical applications are described along with prior art methods of treatment and typical clinical results that demonstrate the need for the new therapeutic devices and methods described herein.

Laryngeal cancer comprises about 3% of all human cancers. The most common treatment for such patients is total laryngectomy which inevitably produces traumatic disability without ruling out tumor recurrence. In spite of great progress made in laryngeal cancer treatment over the past decades (79), five-year survival rates above 90% may be achieved reliably only for earlier stage T1 and T2 disease, whereas five-year survival is less than 60% for patients with intermediate or advanced stage cancers (80). One of the promising new approaches is to apply high-dose-rate brachytherapy from radiation sources placed within a patient-specific biocompatible implant that is itself inserted in the tumor resection cavity at the time of surgery. In a prior method, afterloading catheters were placed into a custom formed tumor bed shaped silicone implant to provide precise computable locations for a high dose rate (HDR) radiation source that was scanned through the catheters to deliver a conformal radiation dose to the tumor bed while the patient is still in the operating room (3, 81). Feasibility of this method of delivering HDR brachytherapy from within afterloading catheters inserted inside a tumor bed shaped silicone implant for intraoperative radiation treatment of laryngeal cancer has been described in the literature (81, 82). However, there are several inherent limitations of afterloading catheters that limit their use in many instances, and require the development of new therapies that can deliver more uniform doses of radiation to the target tissue and whenever possible without catheters exiting through the skin.

Results of a 48 patient pilot study performed in Russia of laryngeal cancers demonstrate the clinical promise of a tumor bed implant method that combines partial larynx resection with sequential high-dose-rate brachytherapy delivered to the resection cavity wall from within an intra-operatively-formed tumor bed fitting silicone gel implant (81, 82). This procedure allowed reduction in the volume of tissue resected and thus higher probability of preserving organ function. To extend the positive results of this organ sparing surgery with brachytherapy implant to more advanced disease, the addition of contact hyperthermia (heating tissue adjacent to a hot surface) is now proposed. (83)

Gliomas are the most commonly occurring brain tumors. Approximately 60% of primary brain tumors are high grade gliomas including Grade IV glioblastoma multiforme (GBM), of which there are approximately 10,000 and 74,000 new cases annually in the US and World respectively. One treatment approach is to implant an array of catheters percutaneously into the GBM and insert radioactive seeds (e.g. I-125) into the catheters for brachytherapy treatment with or without adjuvant hyperthermia applied via miniature coaxial microwave antennas inserted into the same catheters after withdrawal of the brachytherapy seeds. With adjuvant hyperthermia, this approach demonstrated relative success by more than doubling the 2 year local control of GBM treatment with brachytherapy alone from 15 to 31%.(69-71) While the addition of interstitial microwave hyperthermia led to impressive improvement over brachytherapy alone results, the limit of toxicity was reached and overall long term survival for GBM suggests continued search for more effective treatment approaches. Subsequently a new procedure was introduced to resect GBM and implant permanent I-125 seeds directly in the tumor bed at time of surgery and combine with whole brain radiation. Unfortunately this procedure resulted in excessive radiation toxicity and reoperation rates from the direct contact seeds, without demonstrating an improvement in survival.(84) This same approach of permanent I-125 seeds implanted into the resection cavity yielded better results without additional whole brain radiation, (85) but this increased the rate of brain metastasis which subsequently required additional radiation.

In attempts to enhance clinical outcomes, other investigators have attempted multimodality brain tumor treatments. One protocol added chemotherapy with BCNU impregnated wafers to the I-125 radiation seeds placed all around the inside of resection cavity, and again caused too much toxicity from the direct contact radiation seeds and simultaneously released anticancer drug.(25) In contrast, other investigators impregnated biodegradable polymer implants with carmustine,(86) Gliadel,(26) or cyclophosphamide,(87) and implanted them into brain tumor resection cavities for controlled release of chemotherapy. In these later interstitial chemotherapy approaches, there was no toxicity from non-uniform radiation dose distribution and initial results have been promising but still leave considerable room for improvement.

More recently, another short half-life radioactive material (Cs-131) was investigated for its safety and efficacy as a permanently implantable therapeutic. One protocol investigated direct implantation of Cs-131 seeds in seed strands into brain metastasis resection cavities with initially promising results.(88)

In an attempt to smooth out the peaks and valleys of radiation dose around individual seeds or seed strands, another approach was to implant a balloon into the resection cavity filled via a port at the skin surface with an I-125 or Cs-131 based radioactive fluid (e.g. Iotrex or Cesitrex). In this case, more uniform radiation dose was possible over the entire resection cavity wall and initially promising results were obtained when the balloon was used without whole brain radiation.(89)

Adjuvant Hyperthermia

Interstitial hyperthermia may be delivered to a tissue volume via implanted microwave antennas, ultrasound tubular radiators, radiofrequency electrodes, or thermal conduction redistribution of heat within the interior of an array of small diameter thermally hot needles or catheters.(40) All of the interstitial heating approaches except for one require wires, needles, catheters or other connections from outside the patient to apply power and monitor/control the heat treatment. The unique external magnetic field coupled "hot source" technique has been investigated as an adjuvant to interstitial brachytherapy for several decades.(40, 42, 45, 51, 78, 90-93) In an evolution of that approach, "intracavitary contact hyperthermia" has been proposed for heating tissue in combination with intracavitary brachytherapy from a tumor bed silicone implant.(83) This approach consists of thermal conduction heating from a large diameter hot source that fills the resection cavity such that it generates heat more uniformly within the surrounding tumor bed than is possible from the peaks and valleys of heating within an interstitial catheter array implant. In the prior feasibility study, it was proposed to form the implant out of a mixture of silicone with approximately 40% by weight of spherical ferromagnetic balls that would heat due to eddy current losses when immersed in a radiofrequency magnetic field.(82, 83, 94)

The preferred embodiments build off these previous concepts. Rather than restrict the delivery of radiation to tumor bed from radiation seed positions in a limited number of afterloading catheters embedded in the silicone implant, the preferred embodiments will provide significantly improved radiation dosimetry by dispersing the radioactive sources uniformly around and underlying the surface of the device. This separation of tissue from the radioactive seeds by a calculated distance of polymer significantly lowers the dose gradient in the surrounding tumor bed. The preferred embodiments further improve on brachytherapy treatment by adding contact hyperthermia from the large diameter heated cavity implant surface. In one configuration that avoids all undesirable percutaneous connections to the cavity implant, this invention combines the following features:

i) provides brachytherapy from permanently implanted short half-life radioactive seeds, such as Cs-131, which are contained within the implant and remain in tissue delivering their radiation dose slowly over approximately 50 days;

ii) provides nearly uniform temperature of the cavity surface by filling the implant with either ferromagnetic seeds distributed uniformly a fixed distance under the surface, or filling the implant with magnetic material (e.g. spheres, cylinders, magnetic nanoparticles, or magnetic fluid) and coupling energy into the magnetic material by externally applied magnetic field; and iii) eliminates all power and thermal probe connections to the implant and thereby allows repeated hyperthermia sessions following surgery by using magnetic materials with a thermally self-regulating Curie temperature of approximately 45-50° C.

This type of thermal conduction based hyperthermia is akin to ferromagnetic thermoseed hyperthermia treatments reported in the literature (27, 45, 48, 72, 78), except its aim is not to heat the entire tumor volume but rather just a thin rim of at-risk tissue surrounding a tumor resection cavity.

Precise localization of treatment to just the at-risk tumor bed tissue can be achieved using an intraoperatively formed implant to deliver both the brachytherapy and contact hyperthermia.

One of the problems that limited use of traditional high density needle implant arrays is the high temperature gradient near the surface of small diameter thermal sources, which contributes to overheating of tissue directly adjacent to the sources while more distant tissues are not heated sufficiently. As described previously, the temperature gradient near the surface of the implant depends inversely on its radius. This means that a large 1 cm radius implant that fills a resection cavity should produce about 10 times less thermal gradient in surrounding tissue than the small 1 mm radius thermal seeds used in the past clinical studies.(46, 72) Thus, the uniformity of heating around a tumor bed implant loaded with magnetic material should be much improved over the extreme peaks and valleys of temperature found within a multiple catheter ferromagnetic seed implant array of previous clinical trials (45, 48, 54).

Therefore, the use of magnetic materials having an appropriate Curie point temperature in the therapeutic temperature range. Once the heating characteristics of self-thermoregulating Curie point materials are established, entirely non-invasive heat treatments of magnetic tumor bed implants will be possible without any invasive temperature monitoring probes or power connections (55). With appropriate selection of materials having the desired Curie point temperature, the desired treatment temperature will be regulated by the material itself and will not require external monitoring or control of implant temperature.

REFERENCES

1. Sperry S M, Rassekh C H, Laccourreye O, Weinstein G S. Supracricoid partial laryngectomy for primary and recurrent laryngeal cancer. JAMA Otolaryngol Head Neck Surg. 2013 November; 139(11):1226-35.
2. Wilkie M D, Lightbody K A, Pinto R, Tandon S, Jones T M, Lancaster J. Prognostic implications of pathologically determined tumour volume in glottic carcinomas treated by transoral laser microsurgery. Clin Otolaryngol. 2015 December; 40(6):610-5.
3. Obinata K, Ohmori K, Shirato H, Nakamura M. Experience of high-dose-rate brachytherapy for head and neck cancer treated by a customized intraoral mold technique. Radiat Med. 2007 May; 25(4):181-6.
4. Issels R D. Hyperthermia adds to chemotherapy. Eur J Cancer. 2008 November; 44(17):2546-54.
5. Kumar C S, Mohammad F. Magnetic nanomaterials for hyperthermia-based therapy and controlled drug delivery. Advanced drug delivery reviews. 2011 Aug. 14; 63(9):789-808.
6. Baronzio G, Gramaglia A, Fiorentini G. Hyperthermia and immunity. A brief overview. In Vivo. 2006 November-December; 20(6A):689-95.
7. Lee C T, Mace T, Repasky E A. Hypoxia-driven immunosuppression: a new reason to use thermal therapy in the treatment of cancer? Int J Hyperthermia. 2010; 26(3):232-46.
8. Zhou L, Zhang M, Fu Q, Li J, Sun H. Targeted near infrared hyperthermia combined with immune stimulation for optimized therapeutic efficacy in thyroid cancer treatment. Oncotarget. 2016 Feb. 9; 7(6):6878-90.
9. Paulides M M, Bakker J F, Neufeld E, van der Zee J, Jansen P P, Levendag P C, et al. The HYPERcollar: a novel applicator for hyperthermia in the head and neck. Int J Hyperther. 2007 November; 23(7):567-76.
10. Paulides M M, Bakker J F, Linthorst M, van der Zee J, Rijnen Z, Neufeld E, et al. The clinical feasibility of deep hyperthermia treatment in the head and neck: new challenges for positioning and temperature measurement. Phys Med Biol. 2010 May 7; 55(9):2465-80.
11. Valdagni R, Amichetti M. Report of long-term follow-up in a randomized trial comparing radiation therapy and radiation therapy plus hyperthermia to metastatic lymph nodes in stage IV head and neck patients. Int J Radiat Oncol. 1994; 28:163-9.
12. Dewhirst M W, Vujaskovic Z, Jones E, Thrall D. Re-setting the biologic rationale for thermal therapy. Int J Hyperthermia. 2005 December; 21(8):779-90.
13. Sneed P K, Stauffer P R, Li G, Sun X, Myerson R. Hyperthermia. In: Phillips T, Hoppe R, Roach M, editors. Textbook of Radiation Oncology Third Edition. Philadelphia: Elsevier Saunders Co; 2010. p. 1564-93.
14. Dewhirst M W, Stauffer P R, Das S K, Craciunescu O I, Vujaskovic Z. Hyperthermia In: Gunderson L, Tepper J, editors. Clinical Radiation Oncology. 4th ed. Philadelphia: Elsevier; 2016. p. 381-98.
15. Hurwitz M D, Stauffer P R. Hyperthermia, radiation and chemotherapy: the role of heat in multidisciplinary cancer care. Semin Oncol. 2014 December; 41(6):714-29.
16. Repasky E A, Evans S S, Dewhirst M W. Temperature matters! And why it should matter to tumor immunologists. Cancer Immunol Res. 2013 October; 1(4):210-6.
17. Toraya-Brown S, Fiering S. Local tumour hyperthermia as immunotherapy for metastatic cancer. Int J Hyperthermia. 2014 December; 30(8):531-9.
18. Gaber M H, Wu N Z, Hong K, Huang S K, Dewhirst M W, Papahadjopoulos D. Thermosensitive liposomes: extravasation and release of contents in tumor microvascular networks. Int J Radiat Oncol Biol Phys. 1996 Dec. 1; 36(5):1177-87.
19. Kong G, Dewhirst M W. Hyperthermia and liposomes. Int J Hyperther. 1999; 15(5):345-70.
20. Zagar T M, Vujaskovic Z, Formenti S, Rugo H, Muggia F, O'Connor B, et al. Two phase I dose-escalation/pharmacokinetics studies of low temperature liposomal doxorubicin (LTLD) and mild local hyperthermia in heavily pretreated patients with local regionally recurrent breast cancer. Int J Hyperthermia. 2014 August; 30(5):285-94.
21. Landon C, Park J, Needham D, Dewhirst M. Nanoscale drug delivery and hyperthermia: the materials design and preclinical and clinical testing of low temperature-sensitive liposomes used in combination with mild hyperthermia in the treatment of local cancer. The Open Nanomedicine Journal. 2011; 3:38-64.
22. Colombo R, Da Pozzo L F, Salonia A, Rigatti P, Leib Z, Baniel J, et al. Multicentric study comparing intravesical chemotherapy alone and with local microwave hyperthermia for prophylaxis of recurrence of superficial transitional cell carcinoma.[see comment]. Journal of Clinical Oncology. 2003 Dec. 1; 21(23):4270-6.
23. Inman B A, Stauffer P R, Craciunescu O A, Maccarini P F, Dewhirst M W, Vujaskovic Z. A pilot clinical trial of intravesical mitomycin-C and external deep pelvic hyperthermia for non-muscle-invasive bladder cancer. Int J Hyperthermia. 2014 Feb. 3.
24. Gofrit O N, Shapiro A, Pode D, Sidi A, Nativ O, Leib Z, et al. Combined local bladder hyperthermia and intravesical chemotherapy for the treatment of high-grade superficial bladder cancer. Urology. 2004 March; 63(3):466-71.
25. McPherson C M, Gerena-Lewis M, Breneman J C, Warnick R E. Results of phase I study of a multi-modality treatment for newly diagnosed glioblastoma multiforme using local implantation of concurrent BCNU wafers and permanent I-125 seeds followed by fractionated radiation and temozolomide chemotherapy. J Neurooncol. 2012 July; 108(3):521-5.
26. Xing W K, Shao C, Qi Z Y, Yang C, Wang Z. The role of Gliadel wafers in the treatment of newly diagnosed GBM: a meta-analysis. Drug Des Devel Ther. 2015; 9:3341-8.
27. Stea B, Kittelson J, Cassady J R, Hamilton A, Guthkelch N, Lulu B, et al. Treatment of malignant gliomas with interstitial irradiation and hyperthermia. Int J Radiat Oncol Biol Phys. 1992; 24(4):657-67.
28. Amichetti M, Graiff C, Fellin G, Pani G, Bolner A, Maluta S, et al. Cisplatin, hyperthermia, and radiation (trimodal therapy) in patients with locally advanced head and neck tumors: a phase I-II study. Int J Radiat Oncol. 1993; 26:801-7.
29. Arcangeli G, Lombardini P P, Lovisolo G A, Marsiglia G, Piattelli M. Focusing of 915 MHz electromagnetic power on deep human tissues: a mathematical model study. IEEE Trans Biomed Eng. 1984 January; 31(1): 47-52.
30. Gross E J, Cetas T C, Stauffer P R, Liu R L, Lumori M L. Experimental assessment of phased-array heating of neck tumours. Int J Hyperthermia. 1990 March-April; 6(2):453-74.
31. Paulides M M, Bakker J F, Zwamborn A P, Van Rhoon G C. A head and neck hyperthermia applicator: theoretical antenna array design. Int J Hyperther. 2007 February; 23(1):59-67.
32. Canters R A, Wust P, Bakker J F, Van Rhoon G C. A literature survey on indicators for characterisation and optimisation of SAR distributions in deep hyperthermia, a plea for standardisation. Int J Hyperthermia. 2009 November; 25(7):593-608.
33. Van Rhoon G C, Van Der Heuvel D J, Ameziane A, Rietveld P J, Volenec K, Van Der Zee J. Characterization of the SAR-distribution of the Sigma-60 applicator for regional hyperthermia using a Schottky diode sheet. Int J Hyperther. 2003 November-December; 19(6):642-54.
34. Fatehi D, van Rhoon G C. SAR characteristics of the Sigma-60-Ellipse applicator. Int J Hyperther. 2008 June; 24(4):347-56.
35. Al-Bataineh O, Jenne J, Huber P. Clinical and future applications of high intensity focused ultrasound in cancer. Cancer Treat Rev. 2011 Sep. 15.
36. Chen D, Xia R, Chen X, Shafirstein G, Corry P M, Griffin R J, et al. SonoKnife: feasibility of a line-focused ultrasound device for thermal ablation therapy. Med Phys. 2011 July; 38(7):4372-85.
37. Haar G T, Coussios C. High intensity focused ultrasound: past, present and future. Int J Hyperthermia. 2007 March; 23(2):85-7.
38. Viglianti B L, Lora-Michiels M, Poulson J M, Lan L, Yu D, Sanders L, et al. Dynamic contrast-enhanced magnetic resonance imaging as a predictor of clinical outcome in canine spontaneous soft tissue sarcomas treated with thermoradiotherapy. Clin Cancer Res. 2009 Aug. 1; 15(15):4993-5001.
39. Tempany C M, McDannold N J, Hynynen K, Jolesz F A. Focused ultrasound surgery in oncology: overview and principles. Radiology. 2011 April; 259(1):39-56.
40. Stauffer P R, Diederich C J, Seegenschmiedt M H. Interstitial heating technologies. In: Seegenschmiedt M H, Fessenden P, Vernon C C, editors. Thermoradiotherapy and Thermochemotherapy: Volume 1, Biology, Physiology and Physics. Berlin, New York: Springer-Verlag; 1995. p. 279-320.
41. Atkinson W J, Brezovich I A, Chakraborty D P. Usable frequencies in hyperthermia with thermal seeds. IEEE Trans Biomed Eng. 1984 January; 31(1):70-5.
42. Brezovich I A, Atkinson W J, Chakraborty D P. Temperature distributions in tumor models heated by self-regulating nickel-copper alloy thermoseeds. Medical Physics. 1984; 11:145-52.
43. Burton C V, Hill M, Walker A E. The RF thermoseed—a thermally self-regulating implant for the production of brain lesions. Ieee T Bio-Med Eng. 1971; 18:104-9.
44. Kobayashi T, Kida Y, Tanaka T, Kageyama N, Kobayashi H. Magnetic induction hyperthermia for brain tumor using ferromagnetic implant with low Curie temperature. I. Experimental study. Journal of Neuro-Oncology. 1986; 4:175-81.
45. Stauffer P R, Cetas T C, Fletcher A M, DeYoung D W, Dewhirst M W, Oleson J R, et al. Observations on the use of ferromagnetic implants for inducing hyperthermia. IEEE Trans Biomed Eng. 1984 January; 31(1): 76-90.
46. Mack C F, Stea B, Kittelson J M, Shimm D S, Sneed P K, Phillips T L, et al. Interstitial thermoradiotherapy with ferromagnetic implants for locally advanced and recurrent neoplasms. Int J Radiat Oncol. 1993; 27:109-15.
47. Tucker R D, Huidobro C, Larson T, Platz C E. Use of permanent interstitial temperature self-regulating rods for ablation of prostate cancer. J Endourol. 2000; 14(6):511-7.
48. Stauffer P R, Cetas T C, Jones R C. Magnetic induction heating of ferromagnetic implants for inducing localized hyperthermia in deep-seated tumors. IEEE Trans Biomed Eng. 1984 February; 31(2):235-51.
49. Ivkov R. Magnetic nanoparticle hyperthermia: a new frontier in biology and medicine? Int J Hyperthermia. 2013 December; 29(8):703-5.
50. Johannsen M, Thiesen B, Wust P, Jordan A. Magnetic nanoparticle hyperthermia for prostate cancer. Int J Hyperthermia. 2010; 26(8):790-5.
51. Jordan A, Maier-Hauff K. Magnetic nanoparticles for intracranial thermotherapy. Journal of Nanoscience & Nanotechnology. 2007 December; 7(12):4604-6.
52. Oliveira T R, Stauffer P R, Lee C T, Landon C, Etienne W, Maccarini P F, et al. Preclinical Dosimetry of Magnetic Fluid Hyperthermia for Bladder Cancer. Proceedings of SPIE. 2013 Feb. 26; 8584:OD1-10.
53. Petryk A A, Giustini A J, Gottesman R E, Kaufman P A, Hoopes P J. Magnetic nanoparticle hyperthermia enhancement of cisplatin chemotherapy cancer treatment. Int J Hyperthermia. 2013 December; 29(8):845-51.
54. Chin R B, Stauffer P R. Treatment planning for ferromagnetic seed heating. Int J Radiat Oncol Biol Phys. 1991 July; 21(2):431-9.

55. Cetas T C, Gross E J, Contractor Y. A ferrite core/metallic sheath thermoseed for interstitial thermal therapies. Ieee T Bio-Med Eng. 1998; 45(1):68-77.
56. Datta N R, Ordonez S G, Gaipl U S, Paulides M M, Crezee H, Gellermann J, et al. Local hyperthermia combined with radiotherapy and-/or chemotherapy: recent advances and promises for the future. Cancer Treatment Reviews. 2015 November; 41(9):742-53.
57. Overgaard J. Simultaneous and sequential hyperthermia and radiation treatment of an experimental tumor and its surrounding normal tissue in vivo. Int J Radiat Oncol. 1980; 6:1507-17.
58. Overgaard J. The current and potential role of hyperthermia in radiotherapy. Int J Radiat Oncol. 1989; 16:535-49.
59. Huang H S, Hainfeld J F. Intravenous magnetic nanoparticle cancer hyperthermia. Int J Nanomedicine. 2013; 8:2521-32.
60. Jordan A, Wust P, Scholz R, Tesche B, Fahling H, Mitrovics T, et al. Cellular uptake of magnetic fluid particles and their effects on human adenocarcinoma cells exposed to AC magnetic fields in vitro. Int J Hyperthermia. 1996 November-December; 12(6):705-22.
61. Maier-Hauff K, Rothe R, Scholz R, Gneveckow U, Wust P, Thiesen B, et al. Intracranial thermotherapy using magnetic nanoparticles combined with external beam radiotherapy: results of a feasibility study on patients with glioblastoma multiforme. Journal of Neuro-Oncology. 2007 January; 81(1):53-60.
62. Maier-Hauff K, Ulrich F, Nestler D, Niehoff H, Wust P, Thiesen B, et al. Efficacy and safety of intratumoral thermotherapy using magnetic iron-oxide nanoparticles combined with external beam radiotherapy on patients with recurrent glioblastoma multiforme. J Neurooncol. 2011 June; 103(2):317-24.
63. Hynynen K, Clement G. Clinical applications of focused ultrasound-the brain. Int J Hyperthermia. 2007 March; 23(2):193-202.
64. Focused ultrasound is a platform technology that has the potential to transform the treatment of a variety of medical conditions. [Website]: Focused Ultrasound Foundation; 2017 [cited 2017]; Available from: https://www.fusfoundation.org/diseases-and-conditions/overview.
65. Roberts D W, Strohbehn J W, Coughlin C, Ryan T, Lyons B, Douple E, et al. Hyperthermia of brain tumor: the Dartmouth experience. In: Sugahara T, Saito M, editors. Hyperthermic Oncology 1988, vol 2. London: Taylor & Francis; 1989. p. 88.
66. Salcman M, Samaras G M. Interstitial microwave hyperthermia for brain tumors: results of a phase I clinical trial. Journal of Neuro-Oncology. 1983; 1:225-36.
67. Satoh T, Stauffer P R, Fike J R. Thermal distribution studies of helical coil microwave antennas for interstitial hyperthermia. Int J Radiat Oncol. 1988; 15:1209-18.
68. Satoh T, Stauffer P R. Implantable helical coil microwave antenna for interstitial hyperthermia. Int J Hyperther. 1988; 4:497-512.
69. Sneed P K, Gutin P H, Stauffer P R, Phillips T L, Prados M D, Weaver K A, et al. Thermoradiotherapy of recurrent malignant brain tumors. Int J Radiat Oncol. 1992; 23:853-61.
70. Sneed P K, Stauffer P R, McDermott M W, Diederich C J, Lamborn K R, Prados M D, et al. Survival benefit of hyperthermia in a prospective randomized trial of brachytherapy boost+/−hyperthermia for glioblastoma multiforme. International Journal of Radiation Oncology, Biology and Physics. 1998; 40(2):287-95.
71. Sneed P K, Stauffer P R, Gutin P H, Phillips T L, Suen S, Weaver K A, et al. Interstitial irradiation and hyperthermia for the treatment of recurrent malignant brain tumors. Neurosurgery. 1991; 28:206-15.
72. Stea B, et. al., Interstitial irradiation versus interstitial thermoradiotherapy for supratentorial malignant gliomas: a comparative survival analysis. Int J Radiat Oncol Biol Phys. 1994 Oct. 15; 30(3):591-600.
73. Stea B, et al., A comparison of survival between radiosurgery and stereotactic implants for malignant astrocytomas. Acta Neurochir Suppl. 1994; 62:47-54.
74. Deshmukh R, Damento M, Demer L, Forsyth K, DeYoung D, Dewhirst M, et al. Ferromagnetic alloys with curie temperatures near 50° C. for use in hyperthermic therapy. In: Overgaard J, editor. Hyperthermic Oncology 1984, vol 1. London: Taylor & Francis; 1984. p. 599-602.
75. Lilly M B, Brezovich I A, Atkinson W J. Hyperthermia induction with thermally self-regulated ferromagnetic implants. Radiology. 1985 January; 154(1):243-4.
76. Rehman J, et. al,. Ferromagnetic self-regulating reheatable thermal rod implants for in situ tissue ablation. J Endourol. 2002; 16(7):523-31.
77. Cetas T C, Gross E J, Contractor Y. A ferrite core/metallic sheath thermoseed for interstitial thermal therapies. IEEE Trans Biomed Eng. 1998 January; 45(1):68-77.
78. Mack C F, Stea B, Kittelson J M, Shimm D S, Sneed P K, Phillips T L, et al. Interstitial thermoradiotherapy with ferromagnetic implants for locally advanced and recurrent neoplasms. Int J Radiat Oncol Biol Phys. 1993 Sep. 1; 27(1):109-15.
79. Holsinger F C. Swing of the pendulum: optimizing functional outcomes in larynx cancer. Curr Oncol Rep. 2008 March; 10(2):170-5.
80. Rudolph E, Dyckhoff G, Becher H, Dietz A, Ramroth H. Effects of tumour stage, comorbidity and therapy on survival of laryngeal cancer patients: a systematic review and a meta-analysis. Eur Arch Otorhinolaryngol. 2011 February; 268(2):165-79.
81. Vasil'chenko I L, Pastushenko D A, Kuznetsova T A, Polikarpov A F, Magarill J A, Mal'tsev A A, et al., inventors; Method for treating malignant tumors of larynx and laryngopharynx. Russia patent RU 2322199 C1. 2008 April 20, 2008.
82. Vasil'chenko I L, et. al., [Use of local induced hyperthermia in the treatment of malignant tumors]. Vopr Onkol. 2013; 59(2):84-9.
83. Stauffer P, Vasilchenko I, Osintsev A, Rodrigues D, Bar-Ad V, Hurwitz M, et al. Tumor bed brachytherapy for locally advanced laryngeal cancer: a feasibility assessment of combination with ferromagnetic hyperthermia. Biomedical Physics & Engineering Express. 2016; 2:1-12.
84. Chen A M, Chang S, Pouliot J, Sneed P K, Prados M D, Lamborn K R, et al. Phase I trial of gross total resection, permanent iodine-125 brachytherapy, and hyperfractionated radiotherapy for newly diagnosed glioblastoma multiforme. Int J Radiat Oncol Biol Phys. 2007 Nov. 1; 69(3):825-30.
85. Dagnew E, Kanski J, McDermott M W, Sneed P K, McPherson C, Breneman J C, et al. Management of newly diagnosed single brain metastasis using resection and permanent iodine-125 seeds without initial whole-brain radiotherapy: a two institution experience. Neurosurg Focus. 2007 Mar. 15; 22(3):E3.
86. Brem H, Piantadosi S, Burger P C, Walker M, Selker R, Vick N A, et al. Placebo-controlled trial of safety and efficacy of intraoperative controlled delivery by biodegradable polymers of chemotherapy for recurrent gliomas. The Polymer-brain Tumor Treatment Group. Lancet. 1995 Apr. 22; 345(8956):1008-12.
87. Judy K D, Olivi A, Buahin K G, Domb A, Epstein J I, Colvin O M, et al. Effectiveness of controlled release of a cyclophosphamide derivative with polymers against rat gliomas. J Neurosurg. 1995 March; 82(3): 481-6.
88. Wernicke A G, Yondorf M Z, Peng L, Trichter S, Nedialkova L, Sabbas A, et al. Phase I/II study of resection and intraoperative cesium-131 radioisotope brachytherapy in patients with newly diagnosed brain metastases. J Neurosurg. 2014 August; 121(2):338-48.
89. Rogers L R, Rock J P, Sills A K, Vogelbaum M A, Suh J H, Ellis T L, et al. Results of a phase II trial of the GliaSite radiation therapy system for the treatment of newly diagnosed, resected single brain metastases. J Neurosurg. 2006 September; 105(3):375-84.
90. Hand J W, Trembly B S, Prior M V. Physics of interstitial hyperthermia: radiofrequency and hot water tube techniques. In: Urano M, Douple E, editors. Hyperthermia and Oncology, vol 3. Zeist: VSP; 1991. p. 99-134.
91. Handl-Zeller L, editor. Clinical experience of interstitial thermo-radiotherapy using hot-water-perfusion techniques. Berlin, Heidelberg: Springer-Verlag; 1993.
92. DeFord J A, Babbs C F, Patel U H, Bleyer M W, Marchosky J A, Moran C J. Effective estimation and computer control of minimum tumour temperature during conductive interstitial hyperthermia. Int J Hyperther. 1991; 7:441-53.
93. Marchosky J A, Babbs C F, Moran C J, Fearnot N E, DeFord J A, Welsh D M. Conductive, interstitial hyperthermia: a new modality for treatment of intracranial tumors. In: Bicher Hlea, editor. Consensus on Hyperthermia for the 1990s. New York: Plenum Press; 1990. p. 129-43.
94. Osintsev A M, et. al; Method for local induction heating of biological tissues. Russia patent RU 2497489 C1. 2013 Nov. 10, 2013.

What is claimed is:

1. A multimodality simultaneous thermobrachytherapy treatment system comprising:
    an outer biocompatible expandable balloon configured to fill a resection cavity;
    an inner biocompatible expandable balloon disposed within a cavity defined by the outer biocompatible expandable balloon;
    magnetic material capable of insertion within the outer biocompatible expandable balloon for heating a tissue surrounding a resection cavity wall;
    a biocompatible sheath;
    at least a first catheter, a second catheter, and an internal catheter positioned within the biocompatible sheath:
        the first catheter adapted and configured to extend from outside of the patient to an interior of the inner biocompatible expandable balloon to convey a fluid to the interior of the inner biocompatible expandable balloon,
        the second catheter adapted and configured to extend from outside the patient to an interior of the outer biocompatible expandable balloon to convey the magnetic material to the interior of the outer biocompatible expandable balloon, and
        the internal catheter adapted and configured:
            to extend along the biocompatible sheath, from outside of the patient through the interior of the inner biocompatible expandable balloon, and
            for coupling with a remote afterloader for insertion and movement of a radiation source within the internal catheter;
    a collar external to the sheath, the collar comprising suture holes adapted and configured for fixation to a tissue surface external to the patient; and
    a non-contacting induction coil configured to apply a magnetic field surrounding the outer biocompatible balloon simultaneously with the movement of the radiation source within the internal catheter, the magnetic field adapted and configured to be:
        generated external to the patient;
        inductively coupled to and thereby heat the magnetic material to produce a substantially non-ablative temperature distribution of about 40-45° C. for about 30-60 mins in the tissue surrounding the resection cavity wall when the magnetic material is inserted within the outer biocompatible expandable balloon; and
        applied at a frequency in the range of about 50 kHz to about 500 kHz;
    wherein the inner biocompatible expandable balloon and the outer biocompatible expandable balloon are adapted and configured to be used at the same time.

2. The multimodality treatment system of claim 1, wherein the magnetic material comprises one or more selected from the group consisting of: magnetic nanoparticles, magnetic powder, magnetic fluid, and ferroseeds.

3. The multimodality treatment system of claim 1, wherein:
    the magnetic material is a Curie point self-regulating material.

4. The multimodality treatment system of claim 1, further comprising:
    one or more temperature sensors positioned and configured to monitor a temperature of the magnetic material.

5. The multimodality treatment system of claim 4, wherein at least one of the one or more temperature sensors is positioned within the inner or the outer biocompatible expandable balloon.

6. The multimodality treatment system of claim 4, wherein at least one of the one or more temperature sensors is positioned adjacent to a wall of the inner or the outer biocompatible expandable balloon.

7. The multimodality treatment system of claim 1, wherein the magnetic material is within an insertion device.

8. The multimodality treatment system of claim 1, further comprising:
    a remote afterloader coupled with the internal catheter, the remote afterloader programmed to insert and move a radiation source within the internal catheter.

9. A combined hyperthermia and brachytherapy method for the treatment of cancer, the method comprising:
    providing the multimodality treatment system of claim 1;
    introducing the outer biocompatible expandable balloon, the inner biocompatible expandable balloon, and at least the first catheter, the second catheter, and the internal catheter into a resection cavity of a patient such that the at least the first catheter, the second catheter, and the internal catheter extend outside the patient;

coupling the internal catheter to a remote afterloader;
inflating the outer biocompatible expandable balloon to press against a resection cavity wall;
inserting the magnetic material within the outer biocompatible expandable balloon;
applying an external magnetic field to inductively couple energy into the magnetic material, thereby heating tissue surrounding the resection cavity wall; and
controlling the remote afterloader to introduce a radiation source within the internal catheter.

10. The combined hyperthermia and brachytherapy method of claim 9, wherein the applying an external magnetic field step is performed before, while, or after the radiation source is present in a portion of the internal catheter within the resection cavity.

11. The combined hyperthermia and brachytherapy method of claim 9, wherein the applying an external magnetic field step is performed between 1 and 10 times while the radiation source is present in a portion of the internal catheter within the resection cavity.

12. The combined hyperthermia and brachytherapy method of claim 9, wherein the applying an external magnetic field step produces mild hyperthermia in the tissue surrounding the resection cavity wall.

13. The combined hyperthermia and brachytherapy method of claim 9, wherein the applying an external magnetic field step produces thermal ablation of tissue near the resection cavity wall and mild hyperthermia in surrounding tissues.

14. The combined hyperthermia and brachytherapy method of claim 9, wherein the applying an external magnetic field step produces uniform heating of the resection cavity wall.

15. The combined hyperthermia and brachytherapy method of claim 9, wherein the controlling step includes moving the radiation source in a portion of the internal catheter within the resection cavity.

16. The combined hyperthermia and brachytherapy method of claim 9, wherein the resection cavity is located in a region selected from the group consisting of: a head, a neck, a brain, a lung, a breast, a liver, a colon, and an extremity.

17. A multimodality simultaneous thermobrachytherapy treatment system comprising:
a biocompatible expandable balloon adapted and configured to be inflated within a resection cavity of a patient;
magnetic material lying within the biocompatible expandable balloon; and
a biocompatible sheath;
a first fixation collar and a second fixation collar external to the biocompatible sheath, where the first fixation collar is adapted and configured to seal a first end of the biocompatible expandable balloon to a first portion of the biocompatible sheath, and where the second fixation collar is adapted and configured to seal a second end of the biocompatible expandable balloon to a second portion of the biocompatible sheath;
one or more catheters positioned within the biocompatible sheath, the one or more catheters adapted and configured to extend from outside of the patient to an interior of the biocompatible balloon, at least one of the one or more catheters coupled to a remote afterloader;
a radiation source removably within the biocompatible expandable balloon;
a suture collar external to the sheath, the suture collar comprising suture holes adapted and configured for fixation to a tissue surface external to the patient; and
a non-contacting induction coil adapted and configured to apply a magnetic field surrounding the balloon, the magnetic field adapted and configured to be:
generated external to the patient;
inductively coupled to and thereby heat the magnetic material lying within the biocompatible expandable balloon to produce a substantially non-ablative temperature distribution of about 40-45° C. for about 30-60 mins in the tissue surrounding a resection cavity wall simultaneously with delivery of radiation from the radiation source; and
in a frequency range of about 50 kHz to about 500 kHz.

18. A multimodality treatment system comprising:
a biocompatible expandable balloon configured to fill a resection cavity;
a magnetic material capable of insertion within the biocompatible expandable balloon for heating a tissue around the resection cavity; and
a central catheter configured to extend from outside of the patient to an interior of the biocompatible expandable balloon, the central catheter adapted and configured for coupling with a remote afterloader for insertion of a radiation source into an interior of the biocompatible expandable balloon;
the system being characterized by further comprising a non-contacting external induction coil adapted to apply an external magnetic field surrounding the balloon, the magnetic field:
inductively coupling to and thereby heating the magnetic material within the biocompatible expandable balloon to produce a substantially non-ablative temperature distribution of about 40-45° C. for about 30-60 mins in the tissue around the resection cavity simultaneously with delivery of radiation from the radiation source; and
having a frequency in the range of 50 kHz to 500 kHz.

* * * * *